United States Patent [19]
Jacquet et al.

[11] 3,946,035
[45] Mar. 23, 1976

[54] ANTI-INFLAMMATORY POLYMERS, PHARMACEUTICAL COMPOSITIONS CONTAINING THE SAME AND PROCESS FOR PRODUCING SAID POLYMERS

[75] Inventors: Bernard Jacquet, Antony; Christos Papantoniou, Epinay-sur-Seine; Pierre Dufaure; Claude Mahieux, both of Paris, all of France

[73] Assignee: L'Oreal, Paris, France

[22] Filed: June 27, 1973

[21] Appl. No.: 374,060

[30] Foreign Application Priority Data

June 29, 1972 Luxemburg............................ 65622
June 29, 1972 Luxemburg............................ 65621

[52] U.S. Cl................ 260/243 A; 260/85.7; 424/78; 260/295 R; 260/302 R; 260/326.13 R; 260/326.2

[51] Int. Cl.$^2$....................................... C07D 209/18
[58] Field of Search......... 260/326.13 R, 85.7, 88.3, 260/326.13

[56]  References Cited
 UNITED STATES PATENTS 3,535,337  10/1970  Chemerda et al. ............ 260/326.16
3,798,235  3/1974  Yamamoto et al. ........... 260/326.13

*Primary Examiner*—Elbert L. Roberts
*Attorney, Agent, or Firm*—Cushman, Darby & Cushman

[57]   ABSTRACT

A polymer has on its macromolecular chains in the form of a lateral branching an anti-inflammator residue having a carboxylic acid function chemically linked to the macromolecular chains by an intermediate covalent function.

13 Claims, No Drawings

ANTI-INFLAMMATORY POLYMERS, PHARMACEUTICAL COMPOSITIONS CONTAINING THE SAME AND PROCESS FOR PRODUCING SAID POLYMERS

The present invention relates to new polymers usefully employed in the field of pharmaceuticals, to a process for preparing these polymers and to a composition containing the same.

Heretofore it has been proposed to use, as a medicine, certain polymers having in their macromolecular chains, residues or moieties of a therapeutically active material, in an effort to obtain a delayed and prolonged action of this active material, i.e. to achieve a progressive liberation or absorption of the material in the body. Although many diverse types of polymers have been studied in a number of therapeutic areas, until now these studies have not, essentially, provided a truly commercially acceptable product. It has been observed, for instance, that certain of these polymers characterized by having the active material or residue in branched relationship to the polymer chain exhibit essentially no activity even over prolonged periods of time or exhibit an activity lower than that of the active material employed alone, i.e. not in combination with the polymer.

Accordingly these polymers, often called "anti-inflammatory polymers", i.e. polymers having in the form of a branching relative to the main polymer chain a known anti-inflammatory active material, have not until now proved to be of any sustantial therapeutic significance.

Among the numerous active anti-inflammatory materials currently known and used in the field of therapeutics, certain ones exhibit quite remarkable activity. However, their use is often accompanied by a number of disadvantages, which seriously limit their use.

This is particularly true with respect to such anti-inflammatory materials as 1-(p-chlorobenzoyl)-5-methoxy-2-methyl 3-indole acetic acid (indomethacine), 3'-trifluoromethyl-2-diphenylamine carboxylic acid (flufenamic acid), 2', 3'-dimethyl 2-diphenylamine caroxylic acid (mefenamic acid), 2-(10-methyl-2 phenothiazinyl) acetic acid or (methiazinic acid) and 3'-trifluoromethyl-2-phenylamino 3-pyridine carboxylic acid (niflamic acid) all of which, while exhibiting rapid anti-inflammatory activity after absorption by or topical application onto the body, nonetheless also exhibit relatively high toxicity characteristics. It has been observed that numerous ones of known active materials of this type are ulcerative and accordingly their use is not without certain risks. Consequently a great number of patients cannot be treated with strong anti-inflammatory agents and often there is no substitute which can be prescribed.

It has now been found, however, that it is possible to obtain a delayed and prolonged action of an active anti-inflammatory material and to reduce considerably its toxicity and the ulcertative action by using as the anti-inflammatory active compound certain polymers having in branched relationship to their main chain residues of certain known active anti-inflammatory materials.

Further, when taken orally by a human the activity of the anti-inflammatory polymers of this invention is, in most instances, greater than that of the anti-inflammatory material alone, i.e. not linked to a polymer.

When taken or administered topically to a human, the activity manifests itself in the same order of magnitude, and the polymers exhibit essentially no undesirable side effects, whereas the same anti-inflammatory material alone, when applied topically, has at times been found to produce a significant mortality rate in laboratory animals.

The present invention thus relates to a polymer having in its macromolecular chains in the form of a lateral branching, the residue of an anti-inflammatory material having a carboxylic acid function which residue is linked chemically to said macromolecular chains by an intermediate covalent function. The new polymers according to the invention have an average molecular weight between about 2,000 and 1,000,000. The macromolecular chains of the polymers according to the present invention can be homopolymers, that is, they can result from the polymerization of but one monomer or they can be copolymers, such as bipolymers, terpolymers, etc. that is they can result from the polymerization of at least two ethylenically unsaturated monomers. In copolymers which are formed from at least two different monomers, only one of the monomeric units carries as a branched substituent the residue of the anti-inflammatory material.

The other monomer, or monomers, in this embodiment where the macromolecular chains are constituted from more than two monomers, is generally selected depending upon the desired use of the resulting polymer.

It is thus possible to impart to the polymers of this invention different properties which can depend only on the nature of the one or another of monomers constituting the macromolecular chains of these copolymers.

Representative monomers usefully employed in the present invention include:

vinyl esters of fatty acids having 8–18 carbon atoms, such as vinyl stearate, vinyl octanoate, vinyl dodecanoate and vinyl decanoate;

acrylates and methacrylates of fatty alcohols having 8–18 carbon atoms, such as octyl, dodecyl or octadecyl acrylate and methacrylate, allylic and methallylic esters of an acid having 2–18 carbon atoms such as allyl and methallyl acetates, propionates, butyrates, hexanoates, octanoates, decanoates, dodecanoates, octadeconoates and eicosanoates, the acrylates and methacrylates of N,N-dialkylaminoalkyls such as dimethylaminoethyl methacrylate or diethylaminoethyl methacrylate which can optionally be quaternized, and vinyl heterocycles such as N-vinyl pyrrolidone and the N-acryloyl and methacryloyl D-glucosamines.

Certain of these monomers, such as N-vinyl pyrrolidone, increase the solubility of the resulting polymer in aqueous solutions while others of these monomers having fatty chains increase the solubility of the resulting polymer in an oil vehicle.

Thus it can be seen that by judiciously selecting one or more monomers, it is possible with the use of but one anti-inflammatory material to produce either an aqueous composition or in oily compositions, a feature which heretofore was not always possible with the anti-inflammatory materials alone, that is, not fixed on polymer chains.

As indicated above, the residue of the anti-inflammatory material is linked to the macromolecular chains of the polymer by an intermediate covalent function.

According to a first embodiment of the present invention, the polymers are homopolymers, that is they are constituted by repeating units selected from the group consisting of:

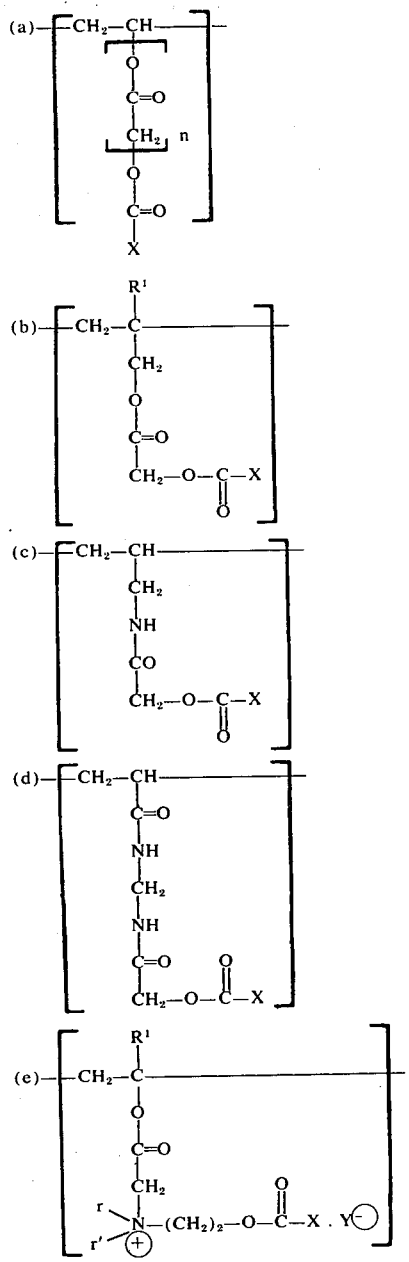

wherein:
n is 1–10, preferably 1–3 inclusive,
R¹ represents hydrogen or methyl,
r and r' represent alkyl having 1–3 carbon atoms,
Y represents chlorine or bromine, and
X represents aryl, alkaryl or aromatic heterocycle residue derived from an anti-inflammatory material.

According to a second embodiment of the present invention, the polymers are bipolymers having repeating units of the formula

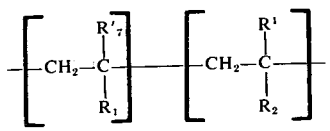 (VI)

wherein:
R¹ represents hydrogen or methyl,
R'₇ is hydrogen or methyl
R₁ represents a member selected from the group consisting of a.

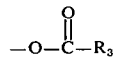

wherein R₃ represents a saturated hydrocarbon chain having 8–18 carbon atoms, b.

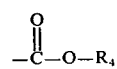

wherein R₄ represents either a saturated hydrocarbon chain having 8–18 carbon atoms, or N,N'-dialkylaminoethyl wherein said alkyl moieties have 1–3 carbon atoms, c.

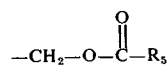

wherein R₅ is a saturated hydrocarbon having 2–18 carbon atoms,

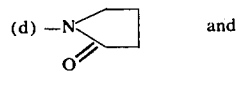

and

R₂ represents a member selected from the group consisting of

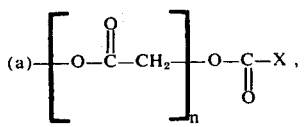

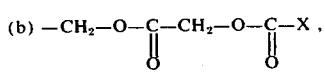

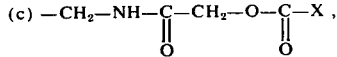

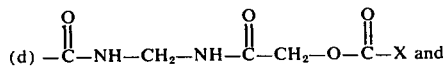

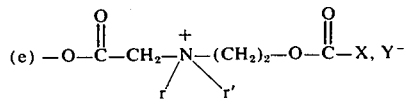

wherein
r and r' represent alkyl having 1–3 carbon atoms,

Y represents chlorine or bromine,
n is 1–10, preferably 1–3 and
X is aryl, alkaryl or aromatic heterocycle residue derived from an anti-inflammatory material.

In accordance with the present invention, the residue of anti-inflammatory material, X, which is fixed onto the macromolecular chains can be selected from the group consisting of:

(1) 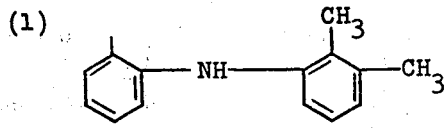

(2) 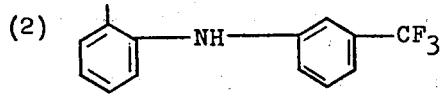

(3) 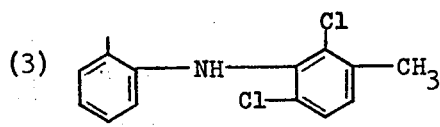

(4) 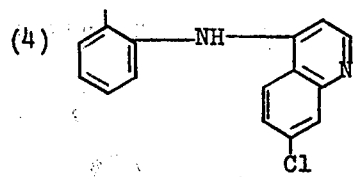

(5) 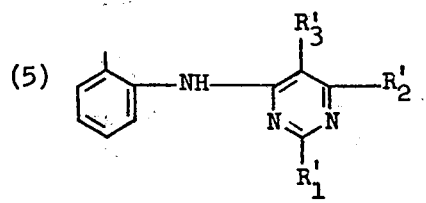

wherein $R'_1$, $R'_2$ and $R'_3$ each independently represent alkyl having 1–3 carbon atoms, Cl, Br, F or I, (6) 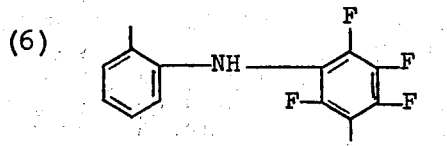

(7) 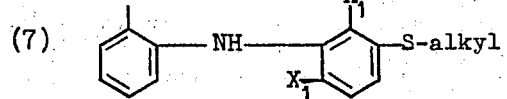

wherein each $X_1$ independently represents Cl Br, F or I and said alkyl has 1–3 carbon atoms.

(8) 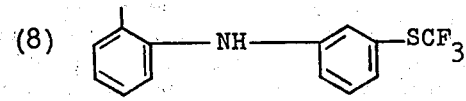

(9) 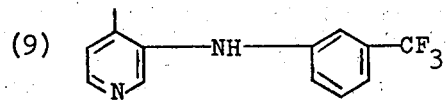

(10) 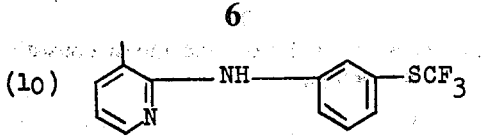

(11) 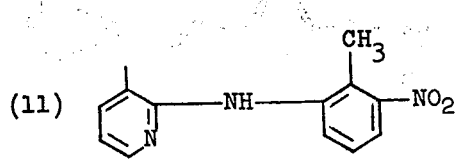

(12) 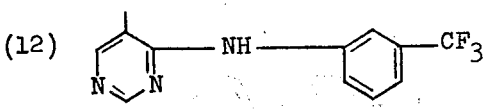

(13) 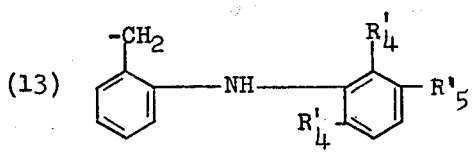

wherein each $R'_4$ independently is selected from the group consisting of hydrogen, chlorine, methyl and methoxy and $R'_5$ is selected from the group consisting of hydrogen, methyl, methoxy and trifluoromethyl,

(14) 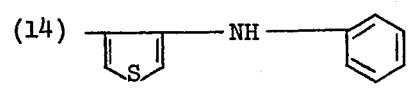

(15) 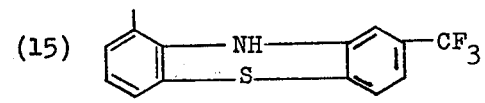

(16) 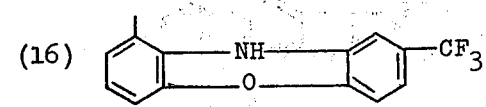

(17) 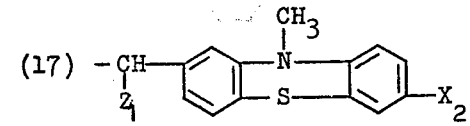

wherein $Z_1$ is selected from the group consisting of hydrogen and methyl and
$X_2$ is selected from the group consisting of hydrogen and methoxy,

(18) 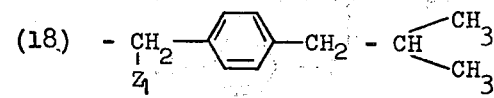

wherein $Z_1$ is selected from the group consisting of hydrogen and methyl,

(19) 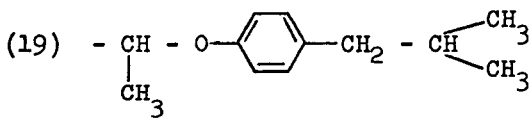

(20) 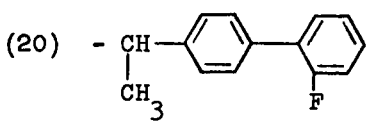

(21) 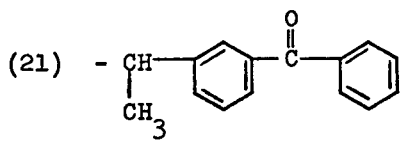

(22) 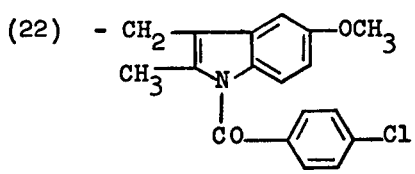

(23) 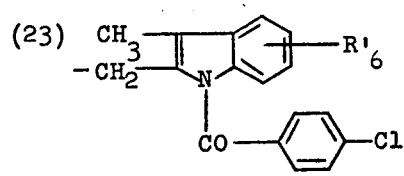

wherein $R'_6$ is selected from the group consisting of methoxy and $-CF_3$ and is in the 5 or 6 position,

(24) 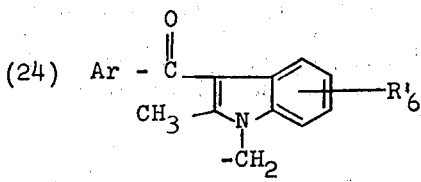

where $R'_6$ is selected from the group consisting of methoxy and $CF_3$ and is in the 5 or 6 position and Ar is selected from the group consisting of phenyl and phenyl substituted with one or more halogens,

(25) 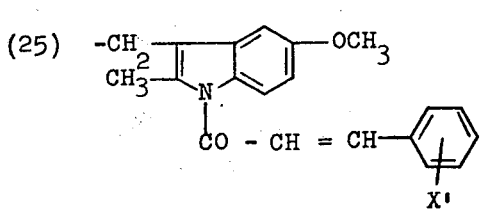

wherein $X'$ is selected from the group consisting of Cl, Br, I and F,

(26) 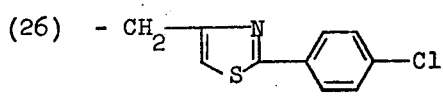

(27) 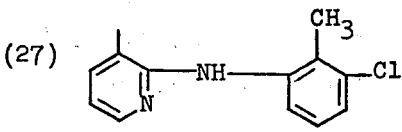

In accordance with the present invention, the polymers have a content of unit substituted by an anti-inflammatory material generally between 10–100% by weight relative to the total weight of the polymer. This content can vary in a sufficiently large measure, depending upon the desired use for the resulting polymer.

The present invention also relates to a process for preparing these anti-inflammatory polymers. Thus, the polymers can be prepared in accordance with two distinct processes.

1. The first process (process 1) consists in homopolymerizing or copolymerizing one or more comonomers having a reactive function which ultimately will permit the formation with an anti-inflammatory material having a carboxylic acid function, the covalent links of the type described above.

After homopolymerization of the monomer or the copolymerization of the comonomers, the resulting homopolymer or copolymer is then reacted with said anti-inflammatory material in amounts sufficient to produce the desired polymer.

2. The second process (process 2), which is preferred, consists in preparing, in a first stage, a monomer from an anti-inflammatory material, said monomer being an "anti-inflammatory monomer", which is then in a second stage homopolymerized or copolymerized with one or more other comonomers.

Representative "anti-inflammatory monomers" include those selected from the group consisting of (a) 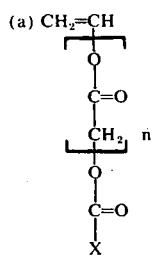 (VII)

(b) 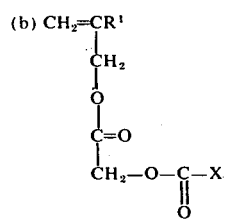 (VIII)

(c) 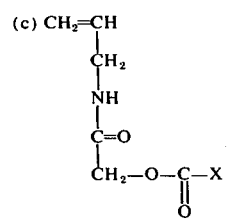 (IX)

and (d) 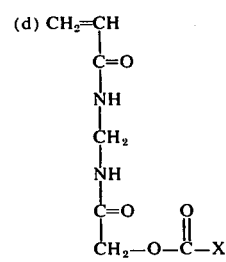 (X)

wherein $n$, $R^1$ and $X$ have the same meaning given above.

In these two processes, the polymerization reactions are the same and can be effected according to conventional polymerization methods, that is, in mass, in solution, in suspension or in emulsion and the polymerization reaction is generally carried out at a temperature between about 50° – 120°C.

The polymerization initiators used are generally conventional free radical polymerization initiators, and the choice of any one particular initiator can depend principally on the different monomers used as well as on the nature of the reaction medium selected.

Representative usable initiators include the peroxides such as benzoyl peroxide, lauroyl peroxide, acetyl peroxide, tertiobutyl hydroperoxide and benzoyl hydroperoxide, a catalyst which, by decomposition, liberates an inert gas such as azobis-isobutyronitrile, an oxidation reduction catalyst such as sodium persulfate, sodium sulfite and $H_2O_2$. The concentration of the initiator is generally between 0.2–35 percent, preferably between 0.5–20 percent, by weight relative to the total weight of monomer content.

The molecular weight of polymers according to the invention can be regulated by introducing during the course of the polymerization reaction small quantities (0.05 to 0.5 weight percent) of a chain regulated agent such as aldehydes, for instance, butyraldehyde or a halogenated substance such as chloroform, bromoform, carbon tetrachloride and the like.

At the end of the polymerization reaction, the polymer obtained can, if desired, be purified by for example, treating it with an ion exchange resin.

Within the framework of the first process defined above, the homopolymerization or the copolymerization of the monomer bearing the reactive function is then followed by esterification or quaternization, these reactions being effected in accordance with conventional methods.

The "anti-inflammatory monomers" of formula (VII) and (VIII) are prepared by reacting the sodium salt of the anti-inflammatory material having a carboxylic acid function with, on the one hand, a compound of the formula

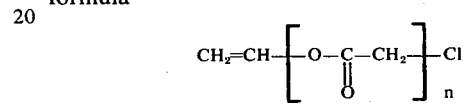

and on the other hand, allyl or methallyl chloroacetate.

The "anti-inflammatory monomers" of formula (IX) and (X) are prepared in the same manner by reacting the sodium salt of the anti-inflammatory material having a carboxylic acid function with N-allyl chloroacetamide and N-(chloromethyl carbonylamino methyl) acrylamide.

The reaction between the sodium salt and the chlorinated compound is preferably carried out in the presence of a solvent such as dimethylformamide, at ambient or elevated temperature.

The quaternary ammonium units such as those of formula (V) are obtained by the quaternization reaction of esters of N,N'-dialkylaminoethyl of the anti-inflammatory material having a carboxylic acid function with a homopolymer or a copolymer having units of the formula

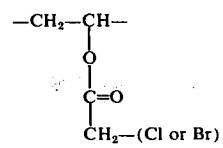

The present invention relates to a new medicine comprising the above described polymers. Preferably, these anti-inflammatory polymers are combined with a pharmaceutically acceptable excipient as well as with pharmaceutical compositions.

Representative pharmaceutical excipients which can be used to provide the pharmaceutical compositions of this invention are those described in U.S. Pat. No. 2,888,380. The pharmaceutical compositions of this invention can be in a form suitable for oral administration, for example, in the form of tablets or pills, aqueous or oily suspensions, dispersible powders or granules, an emulsion, hard or soft capsules, syrups or elixirs.

Thus these orally administrable compositions can be prepared in accordance with any known practical process for the production of pharmaceutical compositions and such composition can contain one or more agents such as sweetening agents aromitizing agents, coloring agents and preservatives in order to provide a suitable pharmaceutical preparation having an agreeable taste.

The pharmaceutical compositions of this invention can also be provided in an appropriate form for topical application, for example, in the form of an ointment, lotion or even in the form of an aerosol.

The ointments and lotions produced with the anti-inflammatory polymers of this invention avoid a rapid migration of the anti-inflammatory material through the skin into the body thereby significantly reducing or minimizing undesirable side effects.

According to a particular embodiment of the present invention, the pharmaceutical compositions can also be provided in the form of an aerosol. In this embodiment, the anti-inflammatory polymer is packaged under pressure in aerosol bombs or containers in an aqueous alcoholic or hydroalcoholic solution, in admixture with a suitable gaseous propellant.

When topically applied to the portion of the body to be treated, there is formed a film which in certain cases can be totally water insoluble thereby permitting contact of the skin with water without interrupting the desired treatment.

The compositions according to the invention can also be provided in the form of wound dressings or in the form of suppositories.

When the pharmaceutical compositions of this invention is administered orally or rectally, the daily dose is about 100 mg to 5 g of anti-inflammatory polymer. However, these daily doses can be varied depending, for instance, on the weight and age of the person being treated.

For topically applied compositions i.e. those in the form of an ointment, lotion or an aerosol, the concentration of the anti-inflammatory polymer is generally between 0.1–10 percent relative to the total weight of the pharmaceutical composition.

Thus the pharmaceutical composition of the invention are effective in the treatment of essentially the same type of inflammations which heretofore were generally treated with the anti-inflammatory material alone.

Among the different symptoms of inflammation that can be treated with the anti-inflammation polymer of this invention are rheumatic disorders, for example articular rhumatism, osteoarthritis and other degenerating disorders of the joints, psoriatic arthritis, gout and rheumatic fever, rhumatism of soft tissue, for example, the tendinites, the periarthrites and the periostites, as well as muscular rhumatism aggravated by example sicatic and the like.

As indicated above, the anti-inflammatory copolymers of the present invention are particularly desirable when orally administered since their activity is not immediate but rather prolonged over a period of time thereby advantageously permitting the spacing of the number of doses to be administered while achieving uninterrupted treatment.

However, one of the most important characteristics of the polymers of this invention is their absence of toxicity while having excellent anti-inflammatory activity. Consequently, with the use of these polymers it is possible to administer relatively high doses so as to secure the desired efficacious results without fear of undesirable side effects.

Finally, contrary to certain known anti-inflammatory agents, the polymers of this invention have no influence on inhibiting the formation of prostaglandine and thus can be prescribed to pregnant women without fear of significant delay in their delivery.

The present invention also relates to a process for treating inflammations, this process consisting in administering orally or topically to the inflamed area, a pharmaceutical composition of the invention.

The following examples are given to illustrate the invention.

EXAMPLES OF PREPARING POLYMERS

Example 1

Preparation of a copolymer of N-vinylpyrrolidone/ [1-(p-chlorobenzoyl)-2-methyl-5-methoxy] 3-indole vinyloxy carbonyl methyl acetate (process 1).

a. Preparation of copolymer of N-vinylpyrrolidonevinyl choroacetate.

Into a 1 liter flask provided with a condenser filled with solid carbon dioxide, a nitrogen inlet tube, a dropping funnel and a mechanical agitator, there are introduced 1 g of azobis-isobutyronitrile in solution in 100 g of absolute ethanol, 63.2 g of N-vinylpyrrolidone and 36.8 g of vinyl chloroacetate.

The solution is heated to 80°C for 9 hours with agitation. After a period of one hour of the polymerization reaction, the reaction mixture thickens. There is then introduced through the dropping funnel 200 ml of absolute ethanol over a period of one hour.

The polymer is obtained in the form of a powder by pouring the ethanolic solution in sulfuric ether. Then the polymer is redissolved in ethanol and reprecipitated in sulfuric ether, filtered and dried at 40°C under reduced pressure.

Yield — 75% — average molecular weight = 40,000 by osmometry in solution in dioxane.

Elementary analysis shows that the copolymer contains 34% vinyl chloroacetate and 66% N-vinylpyrrolidone.

b. Preparation of sodium salt of indomethacine.

Into a 1 liter flask provided with a condenser, a dropping funnel and a nitrogen lead in tube, there are introduced 8.4 g of sodium hydride (58% suspension in oil) and 200 ml of anhydrous dimethyl formamide. There is then slowly introduced, with agitation, a solution of 71.5 g of 1-(p-chlorobenzoyl)-2-methyl-5-methoxy indole acetic acid (indomethacine) in 300 ml of dimethylformamide. At the end of the addition, the temperature is held at 50°C for 1 hour on an oil bath, after which it is cooled. The solution is then left to stand at rest overnight.

c. Reaction of the sodium salt of indomethacine with the copolymer of N-vinylpyrrolidone-vinyl chloroacetate.

72 g of the copolymer prepared in accordance with paragraph (a) above are put into solution in 400 g of dimethylformamide. This solution is introduced into the flask containing the sodium salt of indomethacine. The resulting mixture is then heated on an oil bath to 50°C for 24 hours. The reaction product is then poured, little by little, into 5 liters of water. The resulting white precipitate is filtered, dissolved in acetone and precipitated in sulfuric.

The polymer thus obtained is dried at 40°C under reduced pressure.

Yield — 80% (MW = 42,000)

$\lambda$ max 1 = 320 millimicrons $\lambda$ max 2 = 265–270 millimicrons in solution in a 2:1 mixture of EtOH:CHCl₃

Analysis found:
| | | |
|---|---|---|
| C | 61.52 % | |
| H | 5.97 % | |
| N | 6.34 % | |
| Cl | 4.95 % | |

The analysis shows that 50% of the indomethacine is fixed on the copolymer which corresponds to 62% of anti-inflammatory monomer units present in the polymer.

The polymer can be purified by treating it with an ion exchange resin.

Example 2

Preparation of vinyloxy-carbonylmethyl-[1-(para-chlorobenzoyl)-2-methyl-5-methoxy]-3-indole acetate of the formula

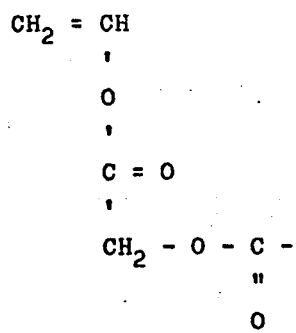

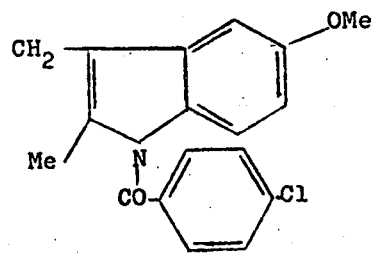

17 g of 1-(p-chlorobenzoyl)-2-methyl-5-methoxy-3-indole acetic acid are dissolved in 50 ml of dimethylformamide and the resulting solution is introduced, little by little, under nitrogen and with agitation, in a suspension of 2.1 g of sodium hydride (58% suspension in oil) in 50 ml of dimethylformamide.

The reaction is exothermic and the temperature is maintained below 50°C. After having left stand for 24 hours the solution obtained at ambient temperature, there are then added 6 g of vinyl chloroacetate and the resulting mixture is left to stand for 24 hours at ambient temperature. This mixture is then poured into 2 liters of water and subsequently extracted with ether. The organic phase is then washed with N/10 sodium hydroxide and water and finally dried on anhydrous sodium sulfate. After evaporation of the ether under reduced pressure, the residue is dissolved hot in a 4:1 mixture of heptane:ethanol. After cooling, the desired compound precipitates in the form of crystals.

Weight obtained: 10.5 g; melting point: 93°C.

| Analysis | Calculated | Found |
|---|---|---|
| C | 62.51 | 62.21 |
| H | 4.57 | 4.89 |
| N | 3.17 | 3.39 |
| Cl | 8.02 | 8.43 |

Example 3

Preparation of a copolymer of vinyl stearate-vinyloxy-carbonylmethyl-[1-(p-chlorobenzoyl)-2-methyl-5-methoxy]-3-indole acetate (Process 2).

1 g of vinyloxy-carbonylmethyl-[1-(p-chlorobenzoyl)-2-methyl-5-methoxy]-3-indole acetate obtained in accordance with Example 2, 1 g of vinyl stearate and 0.2 g of bisazoisobutyronitrile are dissolved in 2 g of acetone. The solution is heated for 24 hours at 80°C and then left to cool, thereafter the solution is diluted with 4 g of acetone and poured, little by little, into 1 liter of absolute ethanol. The polymer precipitates in the form of a powder and is isolated in a conventional manner, yielding 0.8 g of pure polymer.

Analysis shows 55% of indomethacine is fixed on the copolymer which corresponds to 68% of anti-inflammatory monomer units present in the polymer.

| Analysis: | Found |
|---|---|
| C | 67.72 |
| H | 7.65 |
| N | 2.18 |
| Cl | 5.40 |

Example 4

Preparation of acrylamideo methyl carbamoyl methyl ester of indomethacine according to the following reaction scheme:

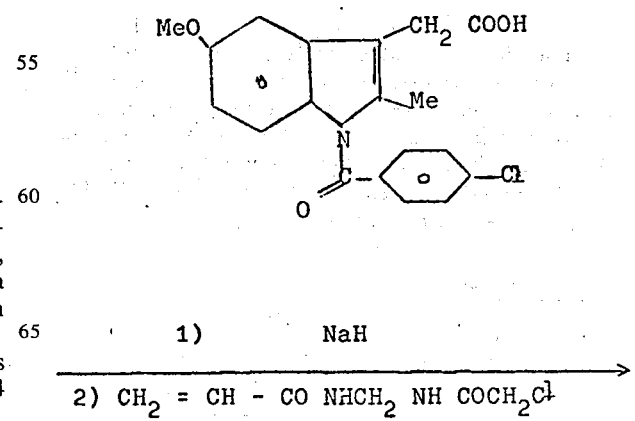

1) NaH

2) CH₂ = CH - CO NHCH₂ NH COCH₂Cl

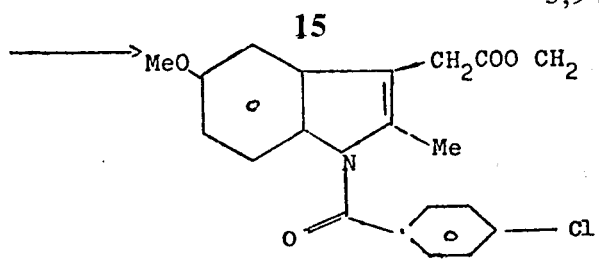

CO NHCH$_2$ NH COCH = CH$_2$

Into a flask there are introduced 40 ml of dimethylformamide and 4.2 g of sodium hydride (58% suspension in oil). The resulting mixture is cooled to 0°C and thereafter there is added, little by little, a solution of 37.6 g of indomethacine in 30 g of dimethylformamide. The resulting mixture is then agitated for 60 hours at ambient temperature at which time there are introduced 17.5 g of N-(chloromethyl carbonyl aminoethyl) acrylamide in solution in 35 ml of dimethylformamide. The mixture is stirred overnight at ambient temperature.

The resulting solution is precipitated in 500 ml of water. The precipitate is taken up in chloroform and washed first with a N/10 NaOH solution and then with water until the wash waters are neutral, after which it is precipitated in lukewarm methanol.

Chromatography on a thin layer (CCM) of the product obtained on Silice LS 254, Schleicher-Schull by using chloroform as the solvent, ethyl acetate as eluent and by developing with U.V and iodide vapors, shows that there is no free indomethacine. There results a 35% yield of the polymer.

Example 5

Preparation of a copolymer of stearyl methacrylate/acrylamidomethyl carbamoyl methyl ester of indomethacine (Process 2).

2 g of the acrylamido methyl carbamoyl methyl ester of indomethacine, produced in accordance with Example 4, are copolymerized with 2 g of stearyl methacrylate in the presence of 0.4 g of azobis-isobutyronitrile in solution in 5 ml of dimethylformamide, for 24 hours at 80°C. The polymer is precipitated in a lukewarm mixture of acetone and methanol.

$\lambda_{max}^{CHCl_3} = 318$ millimicrons

| Analysis: | Found |
|---|---|
| C | 73.18 |
| H | 9.93 |
| N | 1.89 |
| Cl | 0.24 |

Analysis shows that 8% of the indomethacine is fixed onto the copolymer which corresponds to 11 weight % anti-inflammatory monomer units in the polymer.

Example 6

Preparation of allyl carbamoyl methyl ester of indomethacine according to the following reaction scheme:

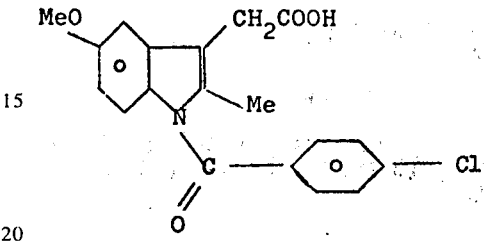

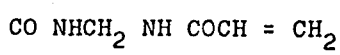

2.1 g of sodium hydride (58% suspension in oil) are mixed with 5 g of dimethylformamide. Into this suspension there is introduced, little by little, a solution of 18 g of indomethacine in 70 g of dimethylformamide.

The resulting mixture is left to stand at rest for 24 hours at which time there are introduced 8.1 g of N-allyl chloroacetamide and the mixture is then heated for 8 hours at 50°C.

The reaction mixture is poured into 500 ml of water, thereby forming a yellow colored oily deposit which crystallizes. After filtering this product, it is dissolved in ethyl acetate and the solution is initially washed with N/2 NaOH and then with water until the aqueous layers are neutral. The organic layers are dried and the ethyl acetate is then distilled off under reduced pressure. The solid residue is recrystallized in isopropanol, yielding 7.5 g of pure product having a melting point of 108°C.
$\lambda_{max}^{CHCl_3} = 320$ millimicrons

| Analysis: | Calculated | Found |
|---|---|---|
| C | 63.35 | 63.30 |
| H | 5.11 | 5.31 |
| N | 6.16 | 6.22 |
| Cl | 7.79 | 8.10 |

Example 7

Preparation of a copolymer of vinyl stearate/allyl carbamoyl methyl ester of indomethacine (Process 2).

2 g of allyl carbamoyl methyl ester of indomethacine, prepared in accordance with Example 6, are copolymerized with 2 g of vinyl stearate in the presence of 0.4 g of azobis-isobutyronitrile in solution in 10 g of acetone.

The solution is heated to reflux for 24 hours at which time the mixture is filtered and the polymer precipitated in 400 ml of methanol, yielding 0.7 g of pure product.
$\lambda_{max}^{CHCl_3} = 317$ millimicrons

| Analysis: | Found |
|---|---|
| C | 71.46 |
| H | 9.10 |
| N | 2.24 |
| Cl | 1.28 |

Analysis shows that 16 percent of the indomethacine is fixed to the copolymer which corresponds to 20 percent anti-inflammatory monomer units in the polymer.

Example 8

Preparation of a copolymer of N-vinylpyrrolidone/-vinyloxycarbonyl methyl flufenamate (Process 1).

a. Preparation of the sodium salt of flufenamic acid.

Into a 1 liter flask provided with a condenser, a dropping funnel and a nitrogen lead in tube, there are introduced 10.4 g of sodium hydride (58% suspension in oil) and 200 ml of anhydrous dimethylformamide. Then, there is slowly introduced, with agitation, a solution of 70.4 g of 3'-trifluoromethyl-2-diphenylamine carboxylic acid (flufenamic acid) in solution in 300 ml of dimethylformamide. At the end of this addition the temperature is held at 50°C for 1 hour using an oil bath at which time it is cooled and left to stand at rest overnight.

b. Reaction of the sodium salt of flufenamic acid with a copolymer of N-vinylpyrrolidone/vinyl chloroacetate.

110 g of the copolymer prepared in accordance with paragraph (a) of Example 1 are put into solution in 400 g of dimethylformamide. This solution is introduced into the flask containing the solution of the sodium salt of flufenamic acid. The mixture is then heated on an oil bath at 50°C for 24 hours. The reaction product is then poured, little by little, into 5 liters of water and the precipitate which forms is filtered, dissolved in acetone and precipitated in sulfuric ether. The resulting polymer is dried at 40°C under reduced pressure.

Yield: 80%
Viscosity: 2.34 cps
$\lambda_{max}^{EtOH} = 288$ millimicrons

| Analysis: | Found |
|---|---|
| C | 60.80 |
| H | 5.88 |
| N | 7.36 |
| F | 7.90 |

Analysis shows that 39% of the flufenamic acid is fixed on the copolymer which corresponds to 50.5 percent of anti-inflammatory monomer units in the polymer. This polymer can be purified by treating it with an ion exchange resin.

Example 9

Preparation of vinyloxycarbonyl methyl flufenamate having the formula

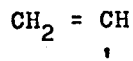
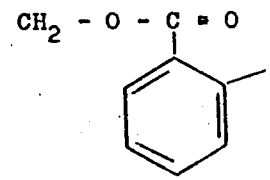
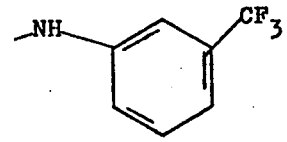

Into a solution of the sodium salt of flufenamic acid, as described in paragraph (a) of Example 8, there are slowly introduced 30 g of vinyl chloroacetate diluted with 100 ml of dimethylformamide. The solution is left to stand for 25 hours at ambient temperature with agitation at which time it is poured, little by little, into 2 liters of water.

The monomer is isolated in the form of a light yellow powder which is recovered and put into solution in sulfuric ether. The solution is washed with N/10 NaOH and then with water until the wash waters are neutral. After drying the ether extract on sodium sulfate, the ether is evaporated under reduced pressure, yielding 60 g of crystalline product which is recrystallized in heptane.

19

Yield: 66%
Melting Point = 61°C
Hexane
λmax 1 = 221 millimicrons
λmax 2 = 285 millimicrons
λmax 3 = 350 millimicrons

| Analysis: | Calculated | Found |
|---|---|---|
| C | 59.19 | 59.42 |
| H | 3.87 | 4.23 |
| N | 3.84 | 3.84 |

Example 10

Preparation of a copolymer of vinyl stearate/vinyloxycarbonyl methyl flufenamate (Process 2).

1 g of vinyloxycarbonyl methyl flufenamate prepared in accordance with Example 9, 1 g of vinyl stearate and 0.2 g of azobis-isobutyronitrile are dissolved in 2 g of acetone. The resulting solution is heated for 24 hours at 80°C, at which time it is cooled and diluted with 4 g of hexane. The resulting solution is then poured, little by little, into 1 liter of absolute ethanol when the polymer precipitates in the form of a powder which is then isolated in a conventional manner, yielding 1.5 g of pure polymer after drying at 40°C under reduced pressure.

$\lambda_{max}^{CHCl_3}$ = 288 millimicrons

| Analysis: | Found |
|---|---|
| C | 67.60 |
| H | 7.21 |
| N | 2.13 |
| F | 7.62 |

Analysis shows that 40% of the flufenamic acid is fixed to the copolymer which corresponds to 52% antiinflammatory monomer units in the polymer.

Example 11

Preparation of a homopolymer of vinyloxycarbonyl methyl flufenamate.

70 g of vinyloxycarbonyl methyl flufenamate, obtained in accordance with Example 9, and 3.5 g of azobis-isobutyronitrile are dissolved in 70 g of acetone. The solution is heated to 80°C for 18 hours at which time there are introduced an additional 3.5 g of azobis-isobutyronitrile. The resulting solution is heated for an additional 24 hours at the same temperature. The solution is then diluted with 140 ml of acetone, filtered and poured into 2 liters of absolute ethanol. The polymer which precipitates is recovered in the form of a white powder which is then dissolved in 250 ml of dioxane. This solution is added to 2 liters of absolute ethanol previously held at a temperature of 50°C. The polymer precipitates on cooling, is filtered and then dried under reduced pressure, yielding 58 g of pure product, having an average molecular weight of 18,500 (toluene).

Example 12

Preparation of acetyl-oxy-methyl-carbonyl-oxy-vinyl acetate flufenamate according to the following reaction:

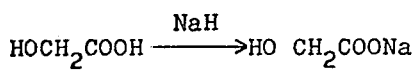

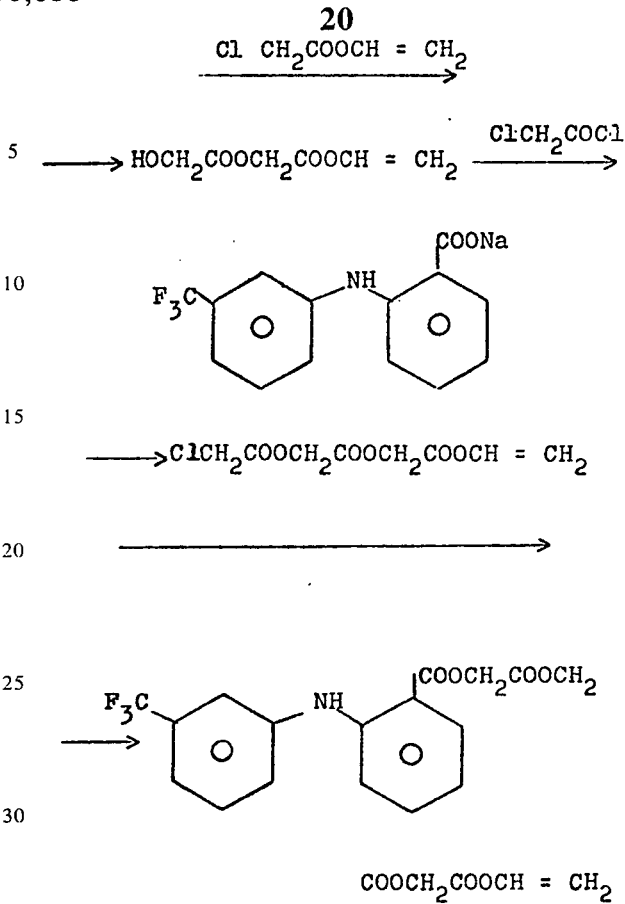

Into a mixture of 8.2 g of sodium hydride (58% suspension in oil) and 8 g of dimethylformamide, there is added, little by little, a solution of 15 g of glycolic acid in 60 g of dimethylformamide.

This mixture is heated with agitation at 50°C for 24 hours. It is then cooled after which there are introduced 25 g of vinyl chloroacetate. The mixture is left to stand with agitation for 24 hours at ambient temperature at which time it is cooled with ice and then into which there are introduced 22.5 g of chloro acetyl chloride. This mixture is held for 48 hours at ambient temperature.

The mixture is then poured into water and the precipitate which forms is taken up in ethanol and reprecipitated in water and then dissolved in ether. The organic layers are washed with water unti neutral at which time the ether is distilled off under reduced pressure.

4.5 g of a yellow solid are obtained and this product is put into solution in 10 g of dimethylformamide. The resulting solution is then poured, little by little, into a mixture of 0.82 g of sodium hydride (58% suspension in oil) with 26 g of dimethylformamide and 5.6 g of flufenamic acid, previously left at ambient temperature for 24 hours.

Example 13

Preparation of a copolymer of vinyl stearate/acetyl-oxy-methyl-carbonyl-oxy-vinyl acetate flufenamate (Process 2).

1 g of acetyl-oxy-methyl-carbonyl-oxy-vinyl acetate flufenamate, prepared in accordance with Example 12, is copolymerized with 1 g of vinyl stearate in the presence of 0.2 g of azobis-isobutyronitrile in solution in 2 g of acetone by heating the same to reflux for 24 hours.

The solution is taken up with chloroform and the polymer is precipitated by pouring the solution into 500 ml of ethanol, yielding 0.8 g of pure polymer.

$\lambda_{max}^{CHCl_3} = 288$ millimicrons

| Analysis: | Found |
|---|---|
| C | 71.46 |
| H | 9.62 |
| N | 0.90 |

Analysis shows that 18% of the flufenamic acid is fixed on the copolymer, which corresponds to 27 percent anti-inflammatory monomer units in the polymer.

Example 14

Acrylamido methyl carbamoyl methyl ester of flufenamic acid is prepared as follows:

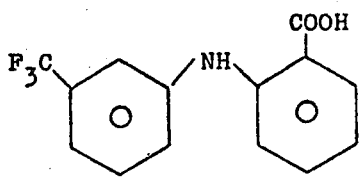

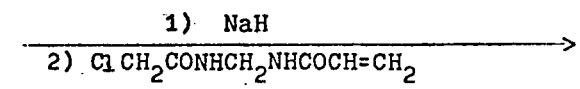

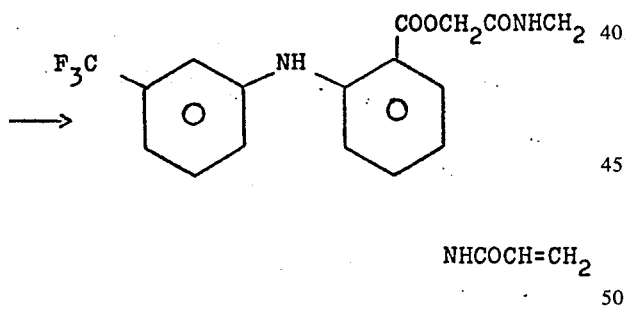

Into a flask containing 40 ml of dimethylformamide there are introduced 4.2 g of sodium hydride (58% suspension in oil). The suspension is cooled to 0°C and there is added thereto, little by little, a solution of 26.6 g of flufenamic acid in 30 g of dimethylformamide. The resulting mixture is held at 50°C for 4 hours at which time there is introduced, little by little, a solution of 17.4 g of N-(chloromethyl carbonylamino methyl) acrylamide in solution in 60 g of dimethylformamide. This mixture is heated at 50°C for 2 hours in the presence of hydroquinone at which time it is left to stand overnight with agitation at ambient temperature.

The product is precipitated in 500 ml of water, filtered, dissolved in hot ethyl acetate, washed with a N/10 NaOH solution and then with water until the aqueous layers are neutral. The ethyl acetate is then distilled off under reduced pressure and the product recrystallized in ethyl acetate, yielding 30 g of pure product, having a melting point of 205°C.

$\lambda_{max\ 1}^{CHCl_3} = 287$ millimicrons
$\lambda_{max\ 2}^{CHCl_3} = 355$ millimicrons

| Analysis: | Calculated | Found |
|---|---|---|
| C | 56.99 | 59.96 |
| H | 4.31 | 4.78 |
| N | 9.97 | 9.80 |
| F | 13.52 | 11.96 |

Example 15

Preparation of a copolymer of stearyl methacrylate/acrylamido methyl carbamoyl methyl ester of flufenamic acid (Process 2).

2 g of acrylamido methyl carbamoyl methyl ester of flufenamic acid prepared in accordance with Example 14, are copolymerized with 2 g of stearyl methacrylate in the presence of 0.4 g of azo-isobutyronitrile in solution in 4 g of dimethylformamide. The reaction mixture is heated for 24 hours at 80°C at which time the polymer is precipitated in lukewarm methanol, yielding 1.5 g of pure polymer.

$\lambda_{max}^{CHCl_3} = 288$ millimicrons

| Analysis: | Found |
|---|---|
| C | 70.01 |
| H | 9.40 |
| N | 3.61 |

Analysis shows that 24.6% of the flufenamic acid is fixed to the copolymer, which corresponds to 36.6% anti-inflammatory monomer units in the polymer.

Example 16

Dimethylamino ethyl ester of flufenamic acid:

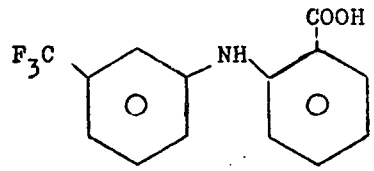

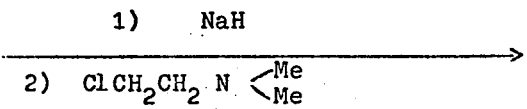

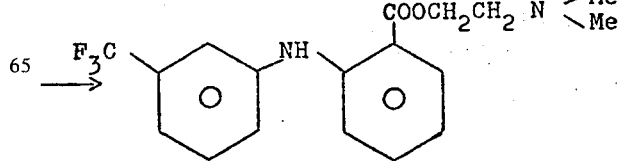

Into a flask there are introduced 0.8 g of sodium hydride (58% suspension in oil), 4 g of dimethylformamide and 5.6 g of flufenamic acid in solution in 20 g of dimethylformamide.

The solution is left to stand with agitation for 4 hours at which time there are introduced 3 g of chloroethyl dimethylamine. The resulting mixture is heated with agitation for 3 hours at 50°C at which time it is then left to stand overnight in the agitation at ambient temperature.

The mixture is poured into water and the oily layer formed is taken up in sulfuric ether. The organic layers are washed with an aqueous N/10 NaOH solution and then with water until neutral. The ether is distilled off under reduced pressure and the oily residue is distilled.

Boiling point: 0.01 mm Hg = 174°C.

6.3 g of product are obtained and used as such.

Chromatography on a thin layer (CCM) on Silice SL 254 Schleicker-Schull with ethanol as solvent, sulfuric ether as eluent and developed with U.V and iodide vapors, show that the product contains no free flufenamic acid.

Example 17

Quaternization reaction between dimethyl amino ethyl ester of flufenamic acid and copolymer of vinyl chloroacetate/N-vinylpyrrolidone (Process 1).

0.89 g of dimethyl amino ethyl ester of flufenamic acid, prepared in accordance with Example 16, is quaternized with 0.375 g of the polymer prepared in accordance with Example 1a, in solution in 5 ml of glutaronitrile and heated for 24 hours at 80°C. The polymer is precipitated by pouring the solution into benzene and then taking it up in glutaronitrile and re-precipitating it twice in benzene, yielding 0.4 g of pure polymer.

$\lambda_{max\ 1}^{CHCl_3} = 287$ millimicrons
$\lambda_{max\ 2}^{CHCl_3} = 355$ millimicrons

| Analysis found: | C | 57.08 |
|---|---|---|
| | H | 6.00 |
| | N | 13.96 |
| | F | 3.20 |

Analysis shows that 15.8% of the flufenamic acid is fixed onto the copolymer which corresponds to 26.5% of anti-inflammatory monomer units present in the polymer.

Example 18

Quaternization reaction between dimethyl amino ethyl ester of flufenamic acid and the copolymer of vinyl chloroacetate/N-vinylpyrrolidone (Process 1).

0.85 g of dimethyl amino ethyl ester of flufenamic acid, prepared in accordance with Example 16, is quaternized with 0.375 g of the polymer prepared in accordance with Example 1a in solution in 5 ml of nitromethane and heated for 24 hours at 80°C.

The polymer is precipitated by pouring the solution into benzene and then taking it up in nitromethane and re-precipitating it two additional times in benzene, yielding 0.45 g of pure polymer.

$\lambda_{max\ 1}^{CHCl_3} = 287$ millimicrons
$\lambda_{max\ 2}^{CHCl_3} = $ millimicrons

| Analysis found: | C | 55.87 |
|---|---|---|
| | H | 5.97 |
| | N | 7.79 |
| | F | 4.10 |

Analysis shows that 20% of flufenamic acid is fixed onto the copolymer which corresponds to 33.5% of anti-inflammatory monomer units present in the polymer.

Example 19

Methallyl oxy carbonyl methyl ester of flufenamic acid is prepared in accordance with the following reaction scheme:

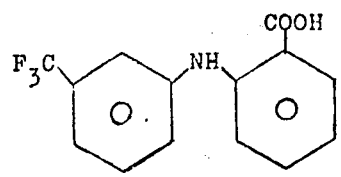

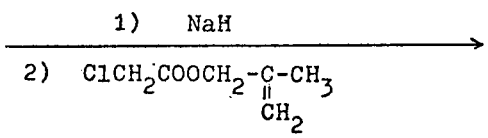

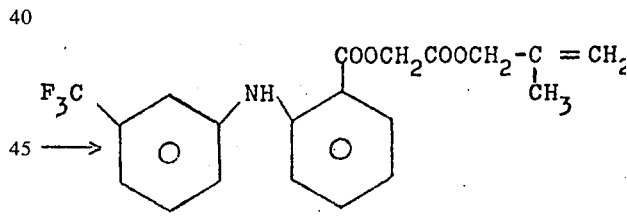

Into a flask there are introduced 40 ml of dimethylformamide and 4.2 g of sodium hydride (58% suspension in oil). The resulting mixture is cooled to 0°C at which time there are introduced, little by little, 28.6 g of flufenamic acid in solution in 30 g of dimethylformamide. The resulting reaction mixture is held at a temperature of 50°C of 4 hours at which time it is then introduced, little by little, into a solution of 14.8 g of methallyl chloroacetate in solution in 10 g of dimethylformamide.

The resulting mixture is then left to stand with agitation overnight at ambient temperature at which time it is then heated for 2 hours at 50°C.

After extraction with ethyl acetate and distillation of the latter under reduced pressure, the product is distilled, yielding one having a boiling point at 0.05 mm Hg of 200°C. The distillation product is dissolved in chloroform, washed with an aqueous N/10 HaOH solution and then with water until the organic layers are neutral.

The chloroform is then distilled under reduced pressure and the product is recrystallized in methanol, yielding 25 g of pure product having a melting point of 42°C.

$\lambda_{max\ 1}{}^{CHCl_3} = 287$ millimicrons
$\lambda_{max\ 2}{}^{CHCl_3} = 355$ millimicrons

| Analysis calculated | | Found |
|---|---|---|
| C | 59.83 | 61.21 |
| H | 4.77 | 5.12 |
| N | 3.67 | 3.52 |

Example 20

Preparation of a copolymer of vinyl stearate/methallyl oxy carbonyl methyl ester of flufenamic acid (Process 2).

2 g of methallyl oxy carbonyl methyl ester of flufenamic acid, prepared in accordance with Example 19, are copolymerized with 2 g of vinyl stearate in the presence of 0.4 g of azobis-isobutyronitrile in solution in 5 g of acetone by heating the same to reflux for 24 hours.

The polymer is precipitated by pouring the solution into ethanol, thus yielding 1.8 g of pure polymer.

$\lambda_{max\ 1}{}^{CHCl_3} = 287$ millimicrons
$\lambda_{max\ 2}{}^{CHCl_3} = 355$ millimicrons

| Analysis found: | C | 69.92 |
|---|---|---|
| | H | 8.71 |
| | N | 1.62 |

Analysis shows that 32% of flufenamic acid is fixed to the copolymer which corresponds to 49% of anti-inflammatory monomer units present in the polymer.

Example 21

Vinyloxy carbonyl methyl ester of 3'-trifluoromethyl thio-2-phenylamino-3-pyridine carboxylic acid is prepared in accordance with the following reaction scheme:

Into a flask there are introduced 0.82 g of sodium hydride (58% suspension in oil) and 2 g of dimethylformamide. The resulting mixture is cooled to 0°C at which time there is introduced, little by little, a solution of 6.3 g of 3'-trifluoromethyl-2-phenylamino-3-pyridine carboxylic acid in 20 g of dimethylformamide.

The resulting reaction mixture is left to stand with agitation for 24 hours at which time there are added 3 g of vinyl chloroacetate. The resulting mixture is left, with agitation, for 24 hours at ambient temperature. The desired product is then precipitated by pouring the said mixture in water and, after filtering the same, the product is taken up in sulfuric ether. The resulting solution is washed with N/2 NaOH and then with water until the was waters are neutral. After distillation of the ether there are obtained 7 g of crystalline residue which is then recrystallized in hexane yielding 4.3 g of pure product having a melting point of 97°C.

$\lambda_{max}{}^{CHCl_3} = 289$ millimicrons

| Analysis: | Calculated | Found |
|---|---|---|
| C | 51.25 | 51.51 |
| H | 3.30 | 3.71 |
| N | 7.03 | 7.00 |
| S | 8.05 | 7.87 |
| F | 14.31 | 15.26 |

Example 22

Preparation of a copolymer of N-vinylpyrrolidone/-vinyloxycarbonyl methyl ester of 3'-trifluoro methyl thio-2-phenylamino-3-pyridine carboxylic acid (Process 2).

1 g of vinyloxycarbonyl methyl ester of 3'-trifluoro methyl thio-2-phenylamino-3-pyridine carboxylic acid, prepared in accordance with Example 21, is copolymerized with 1 g of N-vinylpyrrolidone in the presence of 0.2 g of azobis-isobutyronitrile in solution of 4 g of ethanol at 80°C for a period of 24 hours.

The resulting reaction mixture is diluted by the addition thereto of ethanol, filtered and the resulting polymer is precipitated by pouring the solution into 400 ml of sulfuric ether, yielding 1.2 g of pure polymer.

$\lambda_{max}{}^{CHCl_3} = 288$ millimicrons

| Analysis found: | |
|---|---|
| C | 54.65 |
| H | 6.58 |
| N | 10.23 |
| S | 2.91 |
| F | 4.95 |

Analysis shows that 37% of the 3'-trifluoromethyl thio-2-phenylamino-3-pyridine carboxylic acid is fixed to the copolymer which corresponds to 47% of anti-inflammatory monomer units present in the polymer.

Example 23

Preparation of a copolymer of vinyl stearate/vinyloxycarbonyl methyl ester of 3'-trifluoro methyl thio-2-phenylamino-3-pyridine carboxylic acid (Process 2).

1 g of vinyloxycarbonyl methyl ester of 3'-trifluoromethyl thio-2-phenylamino-3-pyridine carboxylic acid, prepared in accordance with Example 21, is copolymerized with 1 g of vinyl stearate in the presence of 0.2 g of azobis-isobutyronitrile in solution in 4 g of acetone by heating the same to 80°C for a period of 24 hours.

The polymer is precipitated by pouring the solution into 400 ml of absolute ethanol, thus yielding 0.9 g of pure polymer.

$\lambda_{max}^{CHCl_3} = 289$ millimicrons

Analysis found:
C 64.11
H 7.3
N 3.40
S 3.12
F 7.74

Analysis shows that 41% of the acid is fixed on the copolymer which corresponds to 52% of the anti-inflammatory monomer units present in the polymer.

Example 24

Vinyloxycarbonyl methyl ester of 3'-trifluoro methyl thio-2-phenylamino benzoic acid is prepared in accordance with the following reaction scheme:

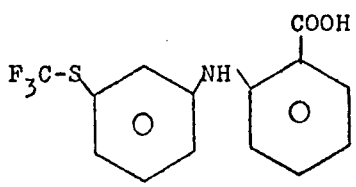

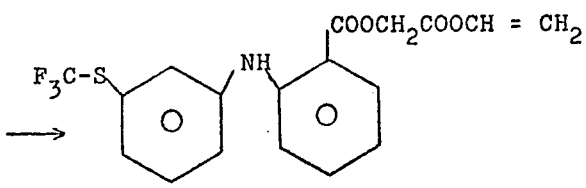

Into a flask there are introduced 0.82 g of sodium hydride (58% suspension in oil) and 2 g of dimethylforamide. The resulting suspension is cooled to 0°C at which time there is introduced, little by little, a solution of 6.3 g of 3°-trifluoromethyl thio-2-phenylamino benzoic acid in 20 g of dimethylformamide. The resulting reaction mixture is left to stand with agitation for a period of 24 hours at ambient temperature at which time there are introduced 3 g of vinylchloroacetate. The resulting mixture is left to stand for 24 hours with agitation at ambient temperature. This suspension is then poured into 400 ml of water and the resulting crystalline precipitate is filtered and then dissolved in sulfuric ether. This etherified solution is then washed with an aqueous solution of N/2 NaOH and then with water until the aqueous layers are neutral.

After distillation of the ether under reduced pressure, there are obtained 5 g of crystalline residue which is then recrystallized in 60 ml of a 95:5 methanol:water mixture, yielding 4.5 g of pure product having a melting point of 42°C.

$\lambda_{max}^{CHCl_3} = 290$ millimicrons

| Analysis: | Calculated | Found |
|---|---|---|
| C | 54.40 | 54.04 |
| H | 3.56 | 3.86 |
| N | 3.52 | 3.86 |
| S | 8.07 | 8.08 |

Example 25

Preparation of a copolymer of N-vinylpyrrolidone/vinyloxycarbonyl methyl ester of 3'-trifluoro methyl thio-2- phenylamino benzoic acid (Process 2).

1 g of vinyloxycarbonyl methyl ester of 3'-trifluoro methyl thio-2-phenylamino benzoic acid, prepared in accordance with Example 4, is copolymerized with 1 g of N-vinylpyrrolidone in the presence of 0.2 g of azobis-isobutyronitrile in solution in 4 g of ethanol by heating the same for 24 hours to reflux.

The solution is diluted with ethanol, filtered and the polymer is precipitated by pouring the solution in 400 ml of sulfuric ether, thus yielding 0.8 g of pure polymer.

$\lambda_{max}^{CHCl_3} = 291$ millimicrons

Analysis found:
C 59.31
H 6.37
N 9.54
S 2.72
F 4.42

Analysis shows that 32% of the 3'-trifluoro methyl thio-2-phenylamino benzoic acid is fixed onto the copolymer which corresponds to 40.5% of anti-inflammatory monomer units present in the polymer.

Example 26

Preparation of a copolymer of vinyl stearate/vinyloxycarbonyl methyl ester of 3'-trifluoro methyl thio-2-phenylamino benzoic acid (Process 2).

1 g of vinyloxycarbonyl methyl ester of 3'-trifluoro methyl thio-2-phenylamino benzoic acid, prepared in accordance with Example 24, is copolymerized with 1 g of vinyl stearate in the presence of 0.2 g of azobis-isobutyronitrile in solution in 4 g of acetone by heating the same to reflux for a period of 24 hours.

The polymer is precipitated by pouring the solution into 400 ml of ethanol, thus yielding 0.9 g of pure polymer.

$\lambda_{max}^{CHCl_3} = 290$ millimicrons

Analysis found:
| | |
|---|---|
| C | 66.36 |
| H | 8.01 |
| N | 1.92 |
| S | 3.71 |

Analysis shows that 44% of the 3'-trifluoro methyl thio-2-phenylamino benzoic acid is fixed onto the copolymer which corresponds to 56% anti-inflammatory monomer units present in the polymer.

Example 27

Vinyloxycarbonyl methyl ester of 2-(4-chloro phenyl)-4-thiazole acetic acid (fenclozic acid) is prepared in accordance with the following reaction sheme:

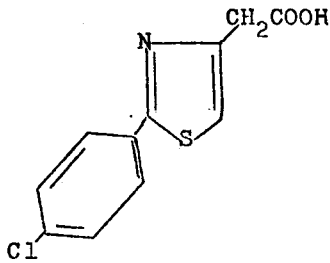

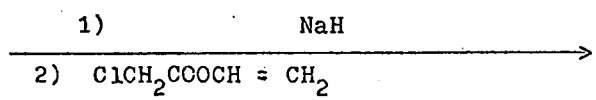

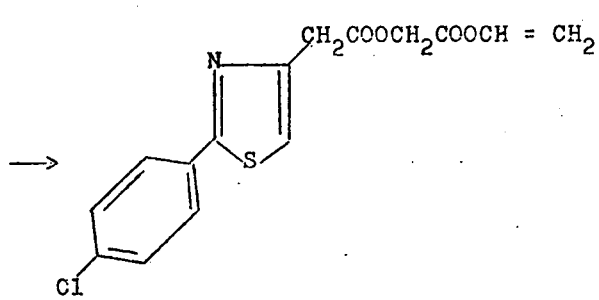

Into a flask containing 4.2 g of sodium hydride (58% suspension in oil) and 40 ml of dimethylformamide, cooled to 0°C, there are introduced, little by little, 2.53 g of fenclozic acid in solution in 30 ml of dimethylformamide. The resulting reaction mixture is left to stand with agitation for a period of 72 hours at ambient temperature at which time there are introduced 1.2 g of vinyl chloroacetate.

This mixture is left to stand at rest for 24 hours at which time it is poured into water. The resulting precipitate is taken up in ether and the solution is then washed with 0.2/N NaOH and then with water until the aqueous layers are neutral. The ether is then distilled off under reduced pressure and the product is crystallized in heptane, yielding 2 g of pure product having a melting point of 83°C.

$\lambda_{max}^{CHCl_3} = 297$ millimicrons

| Analysis: | Calculated | Found |
|---|---|---|
| C | 53.49 | 53.5 |
| H | 3.30 | 3.87 |
| N | 4.16 | 3.96 |
| Cl | 18.53 | 10.04 |
| S | 9.52 | 9.41 |

Example 28

Preparation of a copolymer of stearyl methacrylate/vinyloxycarbonyl methyl ester of fenclozic acid (Process 2).

1 g of vinyloxycarbonyl methyl ester of fenclozic acid, prepared in accordance with Example 27, is copolymerized with 1 g of stearyl methacrylate in the presence of 0.2 g of azobisisobutyronitrile in solution in 5 g of ethanol by heating the same for a period of 24 hours to reflux. The polymer is precipitated by pouring the solution into lukewarm methanol, thus yielding 0.75 g of pure polymer.

$\lambda_{max}^{CHCl_3} = 297\ 7$ millimicrons

Analysis found:
| | |
|---|---|
| C | 68.76 |
| H | 8.03 |
| N | 0.71 |
| Cl | 1.68 |
| S | 1.55 |

Analysis shows that 12.4% of the fenclozic acid is fixed onto the copolymer which corresponds to 16.5 % anti-inflammatory monomer units present in the copolymer.

Example 29

Preparation of a copolymer of vinyl stearate/vinyloxycarbonyl methyl ester of fenclozic acid (Process 2).

0.5 g of vinyloxycarbonyl methyl ester of fenclozic acid, prepared in accordance with Example 27, is copolymerized with 0.5 g of vinyl stearate in the presence of 0.1 g azobisisobutyronitrile in solution in 3 g of acetone by heating the same for 14 hours at reflux. After concentrating the solution, it is then poured into lukewarm methanol, thus yielding 0.6 g of pure polymer.

$\lambda_{max}^{CHCl_3} = 297$ millimicrons

Analysis found:
| | |
|---|---|
| C | 67.03 |
| H | 7.92 |
| S | 2.4 |
| N | 1.1 |
| Cl | 2.66 |

Analysis shows that 19.3% of the fenclozic acid is fixed onto the polymer which corresponds to 25.8% anti-inflammatory monomer units present in the co-polymer.

Example 30

Vinyloxycarbonyl methyl ester of (2'-methyl-3'-chlorophenyl) -2-amino-3-pyridine carboxylic acid (clonixine) is prepared in accordance with the following reaction sheme.

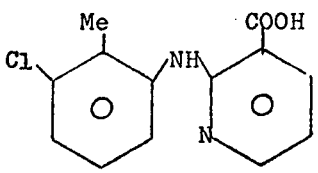

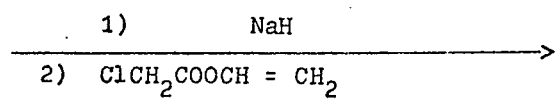

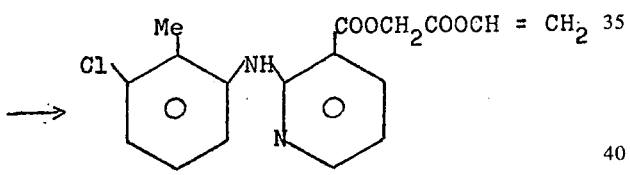

Into a flask there are introduced 0.41 g of sodium hydride (58% suspension in oil) and 1 g of dimethylformamide. The resulting suspension is cooled to 0°C at which point there is then introduced, little by little, a suspension of 2.63 g of clonixine in 15 g of dimethylformamide. The resulting reaction mixture is left to stand for a period of 24 hours with agitation at ambient temperature, at which point there are then introduced 1.5 g of vinyl chloroacetate. The resulting mixture is left to stand for 56 hours with agitation at ambient temperature.

The product is precipitated in the form of crystals by pouring the above mixture into water. After filtering the crystals, the said crystals are dissolved in chloroform and the resulting solution is washed with an aqueous solution of N/10 NaOH and then with water unitl the wash waters are neutral.

The organic layers are dried and the chloroform is distilled off under reduced pressure. There are then recovered 2.8 g of raw product which is recrystallized in 250 ml of a 50:50 mixture of ethanol and methanol, thus yielding 1.3 g of pure product having a melting point of 191°C.

$\lambda_{max}^{CHCl_3} = 332$ millimicrons

| Analysis: | Calculated | Found |
|---|---|---|
| C | 58.87 | 58.28 |
| H | 4.36 | 5.13 |
| N | 8.07 | 8.33 |
| Cl | 10.22 | 10.36 |

Example 31

Preparation of a copolymer of N-vinylpyrrolidone/-vinyloxycarbonyl methyl ester of clonixine (Process 1).

Into a flask containing 0.42 g of sodium hydride (58% suspension in oil) and 2 g of dimethylformamide there is introduced a suspension of 2.63 g of clonixine in 15 g of dimethylformamide.

The resulting mixture is left to stand with agitation at ambient temperature for a period of 24 hours, at which point there are then introduced 4.5 g of N-vinylpyrrolidone-vinyl acetate copolymer, prepared in accordance with paragraph (a) of Example 1. In solution in 15 g of dimethylformamide, the resulting mixture is then heated to 50°C for a period of 24 hours.

The polymer is precipitated by pouring the solution in 500 ml of water and after filtering the polymer and dissolving it in 50 ml of ethanol, the polymer is reprecipitated by pouring the solution into 500 ml of sulfuric ether.

The polymer is then dissolved again in ethanol and reprecipitated one more time in sulfuric ether, thus yielding 2.7 g of pure polymer.

$\lambda_{max}^{CHCl_3} = 335$ millimicrons

Analysis found:
C  57.57
H  6.90
N  11.72
Cl  3.78

Analysis shows that 28% of the clonixine is fixed onto the copolymer which corresponds to 37% anti-inflammatory monomer units present in the polymer.

Example 32

Vinyloxy carbonyl methyl ester of 2',3'-dimethyl-2-diphenylamine carboxylic acid (mefenamic acid) is prepared in accordance with the following reaction scheme:

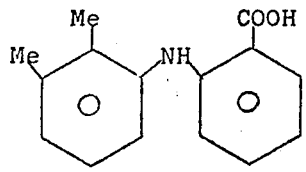

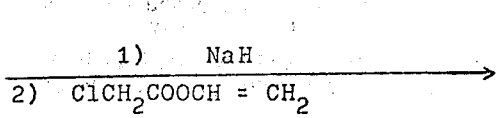

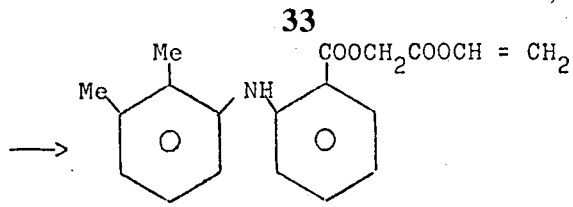

Into a flask containing 0.62 g of sodium hydride (58% suspension in oil) and 2 g of dimethylformamide previously cooled to 0°C there is introduced, little by little, a suspension of 3 g of mefenamic acid in 20 g of dimethylformamide. The resulting suspension is left to stand for 24 hours with agitation at ambient temperature, at which point there are introduced 1.5 g of vinyl chloroacetate and the resulting mixture is left to stand with agitation at ambient temperature for an additional 24 hours.

The product is recovered in the form of crystals by pouring the reaction mixture into 500 ml of water. After filtering the crystals the same are dissolved in sulfuric ether and the organic layers are washed with an aqueous N/2 NaOH solution and then with water until the aqueous layers are neutral.

The sulfuric ether is distilled off under reduced pressure and the residue is recrystallized in methanol, yielding 2.7 g of pure product having a melting point of 87°C.

$\lambda_{max\ 1}^{CHCl_3} = 280$ millimicrons
$\lambda_{max\ 2}^{CHCl_3} = 360$ millimicrons

| Analysis: | Calculated | Found |
|---|---|---|
| C | 70.35 | 70.13 |
| H | 5.60 | 5.92 |
| N | 4.32 | 4.35 |

Example 33

Preparation of a copolymer of N-vinylpyrrolidone/vinyloxycarbonyl methyl ester of mefenamic acid (Process 2).

1 g of vinyloxycarbonyl methyl ester of mefenamic acid, prepared in accordance with Example 32, is copolymerized with 1 g of N-vinylpyrrolidone in the presence of 0.2 g of azobis-isobutyronitrile in solution in 2 g of ethanol.

The reaction mixture is heated for 24 hours at reflux at which time it is then diluted with chloroform, filtered and the polymer is precipitated in 500 ml of sulfuric ether, thus yielding 1 g of pure polymer.

$\lambda_{max\ 1}^{CHCl_3} = 280$ millimicrons
$\lambda_{Max\ 2}^{CHCl_3} = 358$ millimicrons

| Analysis found: | |
|---|---|
| C | 65.22 |
| H | 7.12 |
| N | 8.74 |

Analysis shows that 32% of the mefenamic acid is fixed to the copolymer which corresponds to 43% anti-inflammatory monomer units present in the polymer.

Example 34

Preparation of a copolymer of vinyl stearate/vinyloxycarbonyl methyl ester of mefenamic acid (Process 2).

1 g of vinyloxycarbonyl methyl ester of mefenamic acid, prepared in accordance with Example 32, is copolymerized with 1 g of vinyl stearate in the presence of 0.2 g of azobis-isobutyronitrile in solution in 2 g of acetone.

The resulting reaction mixture is heated to reflux for a period of 24 hours at which time it is then diluted by the addition thereto of chloroform, filtered, and the polymer is then precipitated by pouring the same into 500 ml of ethanol. The polymer is purified by dissolving it in chloroform and by reprecipitating the same three additional times in ethanol, thus yielding 0.5 g of pure polymer.

$\lambda_{max\ 1}^{CHCl_3} = 358$ millimicrons
$\lambda_{max\ 2}^{CHCl_3} = 278$ millimicrons

| Analysis found: | |
|---|---|
| C | 72.32 |
| H | 8.67 |
| N | 2.26 |

Analysis shows that 51% of the mefenamic acid is fixed to the copolymer which corresponds to 68.5% anti-inflammatory monomer units present in the polymer.

Example 35

Vinyl carbonyl methyl ester of 2-(7-methoxy-10-methyl-2-phenothiazinyl)-α-methyl acetic acid (protizinic acid) is prepared in accordance with the following reaction scheme:

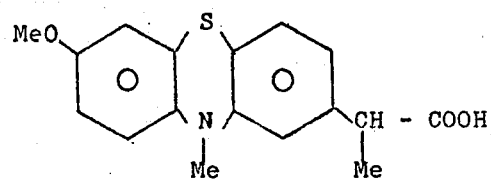

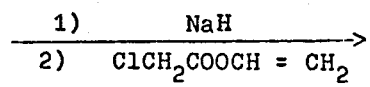

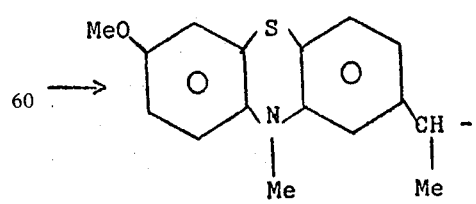

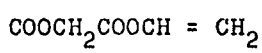

Into a flask containing 0.82 g of sodium hydride (58% suspension in oil) and 2 g of dimethylformamide previously cooled to 0°C, there is introduced, little by little, a solution of 6.3 g of protizinic acid in solution in 15 g of dimethylformamide.

The resulting reaction mixture is left to stand with agitation for a period of 5 hours at ambient temperature at which time there are introduced 3 g of vinyl chloroacetate. The resulting mixture is then left to stand with agitation at ambient temperature for an additional 24 hours. The reaction mixture is then poured into 500 ml of water and extraced with sulfuric ether. It is first washed with an aqueous solution of N/2 NaOH solution and then with water until the aqueous layers are neutral. After distilling off the ether, under reduced pressure, the product is crystallized by dissolving it in a 60:40 lukewarm mixture of methanol and water and then by cooling the said solution, thus yielding 2.8 g of pure product having a melting point of 72°C.

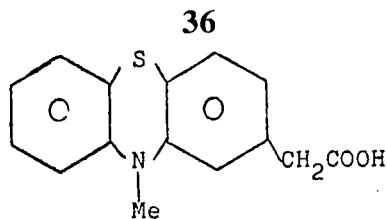

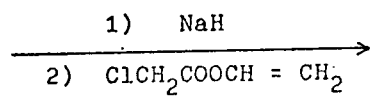

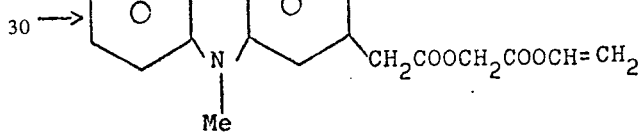

| Analysis: | Calculated | Found |
|---|---|---|
| C | 63.15 | 63.33 |
| H | 5.26 | 5.56 |
| N | 5.50 | 3.25 |
| S | 8.02 | 7.80 |

Example 36

Preparation of a copolymer of vinyl stearate/vinyloxycarbonyl methyl ester of protizinic acid (Process 2). 1 g of vinyloxycarbonyl methyl ester of protizinic acid, prepared in accordance with Example 35, is copolymerized with 1 g of vinyl stearate in the presence of 0.2 g of azobisisobutyronitrile in solution in 4 g of acetone.

The reaction mixture is heated for 24 hours at reflux. The solution is then diluted by the addition thereto of acetone and the polymer is precipitated by pouring the solution into ethanol, thus yielding 0.7 g of pure polymer.

$\lambda_{max\ 1}^{Hexane} = 315$ millimicrons
$\lambda_{max\ 2}^{Hexane} = 257$ millimicrons Analysis found:
C 69.12
H 8.33
N 1.73
S 3.80

Analysis shows that 38.5% of the protizinic acid is fixed to the copolymer which corresponds to 49% anti-inflammatory monomer units present in the polymer.

Example 37

Vinyloxycarbonyl methyl ester of 2-(10-methyl-2phenothiazinyl) acetic acid (methiazinic acid) is prepared in accordance with the following reaction scheme:

Into a flask containing 4.2 g of sodium hydride (58% suspension in water) and 40 ml of dimethylformamide previously cooled to 0°C, there is introduced, little by little, a solution of 2.71 g of methiazinic acid in 12 ml of dimethylformamide.

The resulting reaction mixture is left to stand with agitation for 72 hours at ambient temperature, at which point there are introduced 1.2 g of vinyl chloroacetate. The resulting mixture is left to stand at rest for 24 hours.

The mixture is then poured into water and after extracting with chloroform, the organic layers are washed with an aqueous N/10 NaOH solution and then with water until the wash waters are neutral.

The solution is concentrated and the product precipitated by isopropanol, thus yielding 1.5 ge of pure product in the form of a gum.

| Analysis: | Calculated | Found |
|---|---|---|
| C | 64.20 | 64.09 |
| H | 4.83 | 5.07 |
| N | 3.94 | 3.83 |
| S | 9.02 | 9.24 |

Example 38

Preparation of a copolymer of stearyl methacrylate/vinyloxycarbonyl methyl ester of methiazinic acid (Process 2).

1 g of vinyloxycarbonyl methyl ester of methiazinic acid, prepared in accordance with Example 37, is copolymerized with 1 g of stearyl methacrylate in the presence of 0.2 g of azobis-isobutyronitrile in solution in 5 g of ethanol.

The resulting reaction mixture is heated to reflux for a period of 14 hours at which point the polymer is precipitated by pouring the solution into lukewarm methanol, thus yielding 0.6 g of pure polymer.

| Analysis found: | |
|---|---|
| C | 75.70 |
| H | 11.20 |
| N | 0.68 |
| S | 0.14 |

Analysis shows that 8.9% of methiazinic acid is fixed onto the copolymer which corresponds to 11.7% anti-inflammatory monomer units present in the copolymer.

EXAMPLES OF PHARMACEUTICAL COMPOSITIONS

Example A

In accordance with the present invention, 350 mg of orally administrable tablets are prepared by admixing the following components:

| Polymer of Example 1 | 150 mg |
|---|---|
| Starch | 150 mg |
| Colloidal silica | 40 mg |
| Magnesium stearate | 10 mg |

These tablets administered at a rate of 5 to 6 per day to a subject suffering from osteoarthritis of the knee suppresses all pain after a treatment of 2 weeks.

This example of a pharmaceutical composition is repeated except that the anti-inflammatory polymer of Example 1 is replaced by the same quantity of one of the polymers prepared in accordance with Examples 3, 5, 10, 15, 28, 34 and 36 to provide an equally effective pharmaceutical composition.

Example B

In accordance with the present invention 250 mg of orally administrable tablets are prepared by admixing the following components.

| Polymer of Example 8 | 50 mg |
|---|---|
| Starch | 160 mg |
| Colloidal silica | 35 mg |
| Magnesium stearate | 5 mg |

These tablets, administered at a rate of 4 or 5 per day for a period of 15 days, and then at a rate of 2 to 3 tablets every second day for 2 to 3 weeks provides efficacious treatment for acute articular rhumatism such as sciatica.

This example is repeated except that the anti-inflammatory polymer of Example 8 is replaced by an equivalent quantity of one of the polymers prepared in accordance with Examples 7, 13, 20, 23, 26 and 29 to produce a composition exhibiting comparable effectiveness.

Example C

In accordance with the present invention, a topically applicable pharmaceutical composition for treating inflammations is prepared by admixing the following components:

| Polymer of Example 11 | 500 mg |
|---|---|
| Isopropyl palmitate, q.s.p. | 50 g |

Regular application of this composition on the inflamed area provides a rapid regression of the inflammation.

This example is repeated except that the polymer of Example 11 is replaced by an equivalent quantity of a copolymer made in accordance with one of Examples 3, 8, 13 and 38 to provide an equally effective pharmaceutical composition.

Example D

In accordance with the present invention, a topically applicable pharmaceutical composition for treatment of inflammations is prepared by admixing the following components.

| Polymer prepared in accordance with Example 22 | 400 mg |
|---|---|
| Ethanol, q.s.p. | 50 g |

This composition when applied regularly on the inflamed area checks the inflammation and suppresses the pain.

This example is repeated except that the polymer of Example 22 is replaced by an equivalent quantity of one of the polymers prepared in accordance with one of Examples 17, 18, 31 and 33 to provide an equally effective anti-inflammatory composition.

Example E

In accordance with the present invention, a pharmaceutical composition in the form of a topically applicable aerosol for treating inflammations is prepared by admixing the following components.

| Polymer of Example 25 | 6 g |
|---|---|
| Ethanol. q.s.p. | 100 g |

25 g of this composition are packaged in a conventional aerosol bomb under pressure in the presence of a propellant gas comprising 40 g of dichlorodifluoromethane and 35 g of trichlorofluoromethane. By spraying this composition on the inflamed areas there is obtained a protective film on the inflamed site and when the application is made at a rate of twice a day, there is experienced a clear regression of the inflammation in the case of tendenitis.

Example F

In accordance with the present invention, suppositories which can be administered to persons suffering from articular inflammation are produced by admixing the following components:

| Polymer of Example 28 | 0.3 g |
|---|---|
| Caffeine | 0.1 g |

| | |
|---|---|
| -continued | |
| Purified silica | 0.2 g |
| Coco butter, q.s.p. | 3.5 g |

The administration of 3 to 4 suppositories over a 24 hour period provides excellent regression of the inflammation.

This example is repeated except that the polymer of Example 28 is replaced by an equivalent quantity of one of the polymers prepared according to Examples 3, 10, 20, 23 and 36 to provide an equally effective composition in each instance.

ACTIVITY TESTS OF CERTAIN ANTI-INFLAMMATORY POLYMERS OF THIS INVENTION

The polymers that have been tested are those having as a lateral branching either a residue of indomethacine or a residue of flufenamic acid.

1. Oral Tests

The anti-inflammatory activity of compositions based on the anti-inflammatory copolymers of the present invention, has been studied relative to experimental edema provoked by carragenin.

To this end, male and female Wistar are rats from the same breeding having an average weight of 180 ± 10g are divided into groups of 10 rats each.

Edema is caused by an injection of 0.1 ml of a 1% sterile solution of carragenin in a 0.9% solution of sodium chloride in water. This injection is effected under the plantar surface of the left rear paw of the animal.

For each test, a first group of animals serve as a control group. The difference between the volume of the left rear paw of each animal on which is caused the edema and the initial volume of the same left rear paw serves as a measure of the intensity of the edema. The other groups of animals are submitted to either preventative or curative treatments using on the one hand, the anti-inflammatory polymers of this invention, and on the other hand, known anti-inflammatory materials.

The purpose of these various treatments is to reduce the extent of the edema provoked on the left rear paw of the animal.

The percent reduction of the difference in the volume between the left rear paw of the animals of each group relative to the volume of the left rear paw of the animals of the control group serves as a measure of the efficiency of the various treatments tested.

The anti-inflammatory activity is measured 3 hours, 6 hours, 24 hours and 30 hours, after local injection of the carragenin.

The volume of the animals' paw is measured by dipping the paw in a graduated tube containing mercury. The variation in the height of the mercury serves as a measure of the diminution or increase of the edema.

PREVENTATIVE TREATMENT USING INDOMETHACINE-BASED ANTI-INFLAMMATORY POLYMERS

This treatment occurs 1 hour before the injection of the carragenin.

A first group of rats was treated with 1 ml per 100 g of body weight, of a suspension of 0.5 mg of indomethacine per ml of 1% aqueous solution of carboxymethylcellulose.

A second group of animals was treated with 1 ml per 100 g of body weight, of a suspension of 1 mg of anti-inflammatory polymer, such as was prepared in accordance with Example 1, per ml of a 1% aqueous solution of carboxymethylcellulose.

In the two solutions described above, the concentration of the active substance i.e., indomethacine, is identical.

The results observed are set forth in the following table.

TABLE 1

| Compound | 3 hrs. | 6 hrs. | 24 hrs. | 30 hrs. |
|---|---|---|---|---|
| Indomethacine | 41% | 41% | 44% | 42% |
| Polymer of Example 1 | 0 | 15% | 34% | 67% |

As can be seen, the anti-inflammatory activity of the polymer of this invention manifests itself only 6 hours after the formation of the edema. The intensity of its activity in greater than that of indomethacine at the 30th hour.

On the other hand, indomethacine alone exhibits rapid activity starting from the third hour, and it remains practically constant until the 30th hour.

Preventative treatment using flufenamic acid-based Anti-inflammatory polymers.

This treatment is identical to the preceding treatment, but the first group of rats has been treated with 1 ml per 100g of body weight, of a suspension of 0.5 mg of flufenamic acid per ml of a 1% aqueous solution of carboxymethylcellulose, and the second group of animals was treated with 1 ml per 100g of body weight of a suspension of 1.35 mg of the anti-inflammatory polymer of Example 8, per ml of a 1% aqueous solution of carboxymethylcellulose.

In the two solutions described immediately above, the concentration of the active substance, i.e., flufenamic acid is identical.

The results observed are set forth in the following table.

TABLE 2

| Compound | 3 hrs | 6 hrs | 24 hrs | 30 hrs |
|---|---|---|---|---|
| Flufenamic acid | 36% | 33.5% | 19% | 18% |
| Polymer of Example 8 | 0% | 0% | 20% | 39% |

As can be seen, the anti-inflammatory activity of the polymer of this invention manifests itself only 24 hours after the formation of the edema. The intensity of its activity is greater than that of flufenamic acid alone at the 30th hour.

On the other hand, flufenamic acid alone exhibits rapid activity starting from the third hour and it exhibits a very clear diminution at the 24th hour.

2. Topical Tests

The anti-inflammatory activity of a topically applicable composition based on the anti-inflammatory compositions of the present invention has also been studied relative to abscess provoked by carragenin.

To this end, female Wistar rats from the same breeding having an average weight of 150 ± 10g are divided into groups of 10 rats each.

The abscess is provoked by a sub-cutaneous injection, on the posterior part of the previously shaved back of the rats, of 0.5 ml of a sterile 2% solution of carragenin in a 0.9% solution of sodium chloride in distilled water.

For each test a first group of animals serves as a control group.

The other groups are submitted to preventative or curative treatments using on the one hand, the anti-inflammatory polymers of this invention, and, on the other hand, known anti-inflammatory materials.

So as to measure the extent of the diminution of these abscesses, certain animals are killed 24 hours after injection of the carragenin and others 72 hours after this same injection. Then the weight of the abscesses is determined.

The percent reduction of the weight of the abscesses of the animals treated relative to the control animals is then calculated.

PREVENTATIVE AND CURATIVE TREATMENT USING INDOMETHACINE BASED ANTI-INFLAMMATORY POLYMERS

A first group of rats was treated 24 hours and 3 hours, before injection of carragenin, by applying to the shaved part of the back 0.5 ml of a 5% solution of indomethacine in a mixture consisting of 80% dimethylsulfoxide and 20% water.

Then, another topical application was effected 3 hours after the injection of carragenin.

A second group of rats was preventively and curatively treated in the same way and at the same time intervals with 0.5 ml of 10% solution of the anti-inflammatory polymers of Example 1 in a mixture consisting of 80% dimethylsulfoxide and 20% water.

As was the case in the oral tests, the above two topically applicable solutions tested have the same concentration of the active substance, indomethacine.

The results observed are set forth in Table 3 below.

TABLE 3

| Compound | 24 hours | 72 hours |
|---|---|---|
| Indomethacine | 48% | 66% |
| Polymer of Example 1 | 43% | 0 |

It can thus be seen that the anti-inflammatory activity of the polymer of the present invention is practically identical to that of indomethacine, alone. However, at the 72nd hour the indomethacine is still active whereas the polymer of the present invention exhibits no activity.

It must be remarked that treatment with indomethacine provokes a considerable degree of mortality before the 72nd hour (40% in the animals treated).

Moreover, the autopsy of the remaining animals has shown numerous signs of toxicity, notably some lesions at the level of the stomach and intestine.

On the other hand, no mortality among the rats treated with the polymer of the present invention was noted. Moreover, the autopsy of those rats did not evidence any signs of toxicity.

PREVENTATIVE AND CURATIVE TREATMENT WITH FLUFENAMIC ACID BASED ANTI-INFLAMMATORY POLYMERS

This treatment is identical to that above, but the first group of rats was treated with 0.5 ml of a 5% solution of flufenamic acid in a mixture consisting of 80% dimethylsulfoxide and 20% water, and the second group of rats was preventatively and curatively treated with 0.5 ml of a 13.5% solution of the anti-inflammatory polymer of Example 8, in a mixture consisting of 80% dimethylsulfoxide and 20% water.

As in the oral treatment tests, the above two tested solutions have the same concentration of the active substance, flufenamic acid.

The results observed are set forth in Table 4 below.

TABLE 4

| Compound | 24 hours | 72 hours |
|---|---|---|
| Flufenamic Acid | 26 | 0 |
| Polymer of Example 8 | 25 | 0 |

In accordance with the results shown in Table 4, it can be seen that the anti-inflammatory activity of the polymer of this invention is essentially the same as that of flufenamic acid alone. However, no side effects have been observed with the flufenamic acid based anti-inflammatory polymer.

NON-ULCERATIVE ACTIVITY OF THE ANTI-INFLAMMATORY POLYMER OF THE PRESENT INVENTION

The polymers which have been tested are either the indomethacine bases polymers or the flufenamic acid-based polymers.

The experimental procedure utilized for these tests is that described in the "Journal Pharmacologique", Paris, 1971, 2, 1, 81–83 supplement to No. 1. Fiche technique No. 12.

Procedure

Groups of 9–10 rats weighing 230–250 g. of which one or two groups served as a control group, were put on a water diet 18 hours before the first administration of the product, and were maintained on this diet until the end of the test.

The treatment is daily and lasts 3 days. The products tested are administered in the morning as an aqueous solution or as a suspension, at the rate of 1 ml per 100 g of body weight. The control group received only the carrier.

After the first and the third days, the stomachs of the animals are removed and examined. They were then rated according to the following scheme:

0 — no ulcer
1 — one to two ulcers
2 — three to four ulcers
3 — more than four ulcers The ulceration index for each was then calculated in accordance with the following formula:

$$\frac{\text{Sum of Rating} \times \text{\% of stomachs exhibiting ulcers}}{\text{Number of animals}}$$

Results were obtained after 24 hours and 3 days by comparing, on the one hand the indomethacine and the polymer prepared in accordance with Example 1, and on the other hand the flufenamic acid and the polymer prepared in accordance with Example 11 and these results are set forth in Tables 5 and 6.

Table 5 shows that after a lapse of a sufficiently short period of time (24 hours), indomethacine in particular and to a lesser extent flufenamic acid, exhibited ulcerative activity.

On the other hand, Table 6 shows that the polymer of Example 1 has an ulceration index considerably lower than the index of the control group treated with a placebo and this index is about 20 times lower than that of indomethacine alone and this after 3 days of treatment.

The ulceration index of the polymer of Example 11 is about 2 times greater than that of the control group, however, it is about 7 times lower than that of flufenamic acid alone.

prior to the administration of the product to be tested although drinking water is provided freely.

The polymers of Examples 1 and 8 are administered orally, with an esophagus tube, the polymers being in solution in dimethylsulfoxide ($DM_{50}$), at the following concentrations:

Table 5

| Products | Dose mg/Kg,per os | Number of Animals | (After 24 hours) Rating of the Stomach 0 | 1 | 2 | 3 | Sum of The Ratings | Rats Sick % | Index |
|---|---|---|---|---|---|---|---|---|---|
| Control group receiving only carboxymethylcellulose at 0,5% in water | — | 10 | 10 | | | | 0 | 0 | 0 |
| Indomethacine | 5 | 10 | 3 | 4 | | 3 | 13 | 70 | 91 |
| | 10 | 10 | 2 | 3 | 1 | 4 | 17 | 80 | 136 |
| Polymer of Example 1 | 15 | 10 | 8 | 2 | | | 2 | 20 | 4 |
| | 30 | 10 | 9 | 1 | | | 1 | 10 | 1 |
| Acid flufenamic | 100 | 10 | 7 | 1 | 1 | 1 | 6 | 30 | 18 |
| Polymer of Example 11 | 150 | 10 | 10 | | | | 9 | 0 | 0 |

TABLE 6

| Products | Dose mg/Kg,per os | Number of Animals | (After 3 days) Rating of the Stomachs 0 | 1 | 2 | 3 | Sum of The Ratings | Rats Sick % | Index |
|---|---|---|---|---|---|---|---|---|---|
| Placebo | — | 10 | 7 | 1 | 0 | 2 | 7 | 30 | 21 |
| Indomethacine | 10 | 9 | 0 | 0 | 0 | 9 | 27 | 100 | 300 |
| Polymer of Example 1 | 30 | 9 | 5 | 4 | 0 | 0 | 4 | 40 | 16 |
| Acid Flufenamic | 100 | 10 | 0 | 0 | 0 | 10 | 30 | 100 | 300 |
| Polymer of Example 11 | 150 | 10 | 5 | 3 | 0 | 2 | 9 | 50 | 45 |

Moreover, certain tests carried out in accordance with the procedure of Joudet, Saisas, Philippe and Chermat. Ann. Pharm. Franc. 1968, 26, No. 12, p. 767–770 show that the indomethacine- and flufenamic acid-based anti-inflammatory polymers, when administered to rats having ulcers provoked by the cold (−20°C) do not aggravate the state of the ulcers, which is not the case with indomethacine and flufenamic acid when these substances alone are administered.

ACUTE AND SEMI-CHRONIC TOXICITY OF ANTI-INFLAMMATORY POLYMERS OF THE PRESENT INVENTION

Acute toxicity has been determined principally with regard to the indomethacine- and flufenamic acid-based polymers of Examples 1 and 8 and has been compared to that of indomethacine and flufenamic acid.

The acute toxicity of indomethacine ($DL_{50}$) is as follows:
Mice 90 ± 13 mg/Kg
Rats 32 ± 5 mg/Kg The acute toxicity of flufenamic acid ($DL_{50}$) is as follows:
Mice 1,220 g/Kg
Rats 625 ± 6 mg/Kg The acute toxicity of the polymers of Examples 1 and 8 also have been determined on mice and rats.

The mice are Swiss male and female mice weighing 20 ± 1g and 21 ± 1g. The rats are 5-week old male and female Westar rats, each weighing, respectively, 110 ± 20g and 100 ± 10g.

The animals are divided into lots of 10 (5 males — 5 females) and are given no food for a period of 12 hours 1 g/Kg body weight
2 g/Kg body weight
3 g/Kg body weight The dosage administered is 1 ml per 100g of body weight.

The animals are observed 1 hour after injection and then 96 hours after injection.

No death was observed after the administration of these two types of polymers. Thus they can be considered as nontoxic at these dosages which is quite remarkable taking into account the $DL_{50}$ of the indomethacine, in particular.

The same semi-chronic toxicity is effected in accordance with the same procedure, over 29 days of treatment with polymers prepared in accordance with Examples 1 and 8 at the following daily dosage rates:
15 mg/Kg of body weight for 14 days
30 mg/Kg of body weight for 6 days
50 mg/Kg of body weight for 9 days,
for a total quantity administered for 840 mg/Kg of body weight which caused no mortality of the treated rats.

Weight Developed: No noticeable modification in the weight of the rats has been observed during the treatment.

Hematology: No noticeable variation has been recorded in the hematological results.

Test of Provoked Duiresis: The rate of urinary elimination reveals a very slight variation remaining in the zone compatible with good renal functioning.

Histology: The histological images are normal and only a few modifications occur at the level of the liver of the rats.

Because of the results obtained in the acute toxicity ($DL_0$ at 3 g/Kg then $DL_{50}$ still higher) and in semi-chronic toxicity over a period of a month without manifestation of symptoms of toxicity, macroscopically visible or histologically detectable, it is concluded that the anti-inflammatory polymers of this invention and notably the indomethacine- and flufenamic acid-based polymers are only very slightly toxic.

ACTIVITY OF THE ANTI-INFLAMMATORY POLYMERS ON THE GESTATION PERIOD

This action has been studied by comparing, on the one hand, the indomethacine-base anti-inflammatory polymer of Example 1.

It is known that indomethacine administered to pregnant rats (between the 18th and 21st days of gestation) causes a certain delay in delivery. Consequently, the use of indomethacine is not recommended for pregnant women.

The schedule of tests employed is that described by J. W. Aiken, Nature, Vol. 240, November 3, 1972, pages 21–25.

For indomethacine there were used dosages of 1 mg and 5 mg/Kg of body weight and for the polymer of Example 1, dosages of 3mg and 15 mg/Kg of body weight. The treatment is effected orally at a rate of 1 ml per 100g of body weight. The products are suspended in 0.5% carboxymethyl cellulose.

The results obtained are set forth in Tables 7, 8 and 9 below.

INTERPRETATION OF RESULTS

1. With indomethacine i. At a dosage of 1 mg/Kg of body weight there is observed
   a. no excessive bleeding
   b. a lengthening of the delivery (4 to 5 hours as opposed to 2 to 3 hours for the control group)
   c. nonejection of all foetuses, few in utero deaths
   d. presence of stomach ulcers (2 out of 5)
ii. At a dosage of 5 mg/Kg of body weight there is observed:
   a. excessive bleeding
   b. considerable prolongation of the parturition (3 out of 5 animals) with numerous in utero deaths
   c. even total inhibition causing death without delivery (5 out of 8 animals)
   d. presence of blood in the stomach of all animals 2 With the indomethacine-based anti-inflammatory polymer of Example 1.
i. At a dosage of 3 mg/Kg of body weight there is observed:
   a. no excessive bleeding
   b. no delay in delivery
   c. no foetus mortality
   d. no ulceration
ii. At a dosage of 15 mg/Kg of body weight there is observed the same signs as at a dosage of 3 mg/Kg of body weight.

Because of these results it can be seen that the above polymer of the present invention, compared to indomethacine alone, is significantly more acceptable.

TABLE 7

| | Control: 0.5 % carboxymethylcellulose | | | N=delivery at night | | | |
| Rats | Number of Dosage | Excessive Bleeding | Period of Parturition (hours) | Births | | Foetus in utero | | Ulcers |
| --- | --- | --- | --- | --- | --- | --- | --- | --- |
| | | | | Living | Dead | Living | Dead | |
| 1 | 7 | no | 1.30 | 12 | 0 | 0 | 0 | no |
| 2 | 9 | — | 1.30 | 15 | 0 | 0 | 0 | — |
| 3 | 8 | — | 2.15 | 15 | 0 | 0 | 0 | — |
| 4 | 7 | — | N | 13 | 0 | 0 | 0 | — |
| 5 | 5 | — | N | 11 | 0 | 0 | 0 | — |
| 6 | 5 | — | 2 | 14 | 0 | 0 | 0 | — |
| 7 | 5 | — | N | 9 | 0 | 0 | 0 | — |
| 8 | 5 | — | 2 | 9 | 0 | 0 | 0 | — |
| 9 | 5 | — | N | 9 | 0 | 0 | 0 | — |
| 10 | 5 | — | N | 11 | 0 | 0 | 0 | — |

TABLE 8

| | A) Indomethacine 1 mg/Kg | | | N=delivery at night M=death without delivery 48 hours after control | | | | |
| Rats | Number of Dosages | Excessive Bleeding | Period of Parturition (hours) | Births | | Foetus in utero | | Ulcers |
| --- | --- | --- | --- | --- | --- | --- | --- | --- |
| | | | | Living | Dead | Living | Dead | |
| 1 | 9 | no | N | 10 | 0 | 0 | 0 | yes |
| 2 | 9 | — | >5 | 8 | 0 | 0 | 2 | no |
| 3 | 9 | — | >5 | 16 | 0 | 5 | 0 | no |
| 4 | 9 | — | >4 | 8 | 0 | 6 | 0 | yes |
| 5 | 9 | — | >3 | 8 | 0 | 0 | 0 | no |
| | B) Indomethacine 5 mg/Kg | | | | | | | |
| 1 | 5 | yes | >8 | 1 | 8 | 0 | 3 | yes |
| 2 | 5 | — | >8 | 10 | 4 | 0 | 2 | yes |
| 3 | 5 | — | M | 0 | 0 | | | blood in the stomach |
| 4 | 4 | — | M | 0 | 0 | | | |
| 5 | 5 | — | M | 0 | 0 | | | |
| 6 | 5 | — | M | 0 | 0 | | | |
| 7 | 5 | — | >5 | 1 | 7 | 0 | 3 | yes |
| 8 | 5 | — | M | 0 | 0 | | | |

TABLE 9

| | A) Anti-inflammatory polymer of Example 1 – 3 mg/Kg | | | | | | |
|---|---|---|---|---|---|---|---|
| | | | | Births | | Foetus in utero N=delivery at night | |
| Rats | Number of Dosages | Excessive Bleeding | Period of Parturition (hours) | Living | Dead | Living | Dead | Ulcers |
| 1 | 8 | No | N | 10 | 0 | 0 | 0 | No |
| 2 | 9 | — | 1.30 | 12 | 0 | 0 | 0 | — |
| 3 | 8 | — | 1.10 | 9 | 0 | 0 | 0 | — |
| 4 | 9 | — | N | 16 | 0 | 0 | 0 | — |
| 5 | 7 | — | 2 | 10 | 0 | 0 | 0 | — |
| | B) Anti-inflammatory polymer of Example 1 – 15 mg/Kg | | | | | | | |
| 1 | 5 | No | <2 | 10 | 0 | 0 | 0 | No |
| 2 | 4 | —N | 9 | 0 | 0 | 0 | — | — |
| 3 | 5 | — | <2 | 12 | 0 | 0 | 0 | — |
| 4 | 5 | — | 2 | 10 | 0 | 0 | 0 | — |
| 5 | 5 | — | N | 13 | 0 | 0 | 0 | — |
| 6 | 4 | — | 1.30 | 10 | 0 | 0 | 0 | — |
| 7 | 5 | — | 3 | 11 | 0 | 0 | 0 | — |

What is claimed is:

1. A polymeric compound containing repeating units of the formula

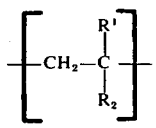

wherein $R^1$ and $R^2$ are selected from the group of values consisting of
   a. $R_2$ is —[O—CO—CH$_2$]$_n$—o—Z,
      $R^1$ is hydrogen and $n$ is 1–10,
   b. $R_2$ is —CH$_2$—O—CO—CH$_2$—O—Z and $R^1$ is hydrogen or methyl,
   c. $R_2$ is —CH$_2$—NH—CO—CH$_2$—O—Z and $R^1$ is hydrogen,
   d. $R_2$ is —CO—NH—CH$_2$—NH—CO—CH$_2$—O—Z and $R^1$ is hydrogen, and
   e. $R_2$ is —O—CO—CH$_2$—N$^+$(CH$_2$)$_2$—O—Z, Y$^{O}$
      with r, r' substituents wherein $r$ and $r'$ represent alkyl having 1–3 carbon atoms, Y represents chlorine or bromine and $R^1$ is hydrogen or methyl, and Z is the acyl residue of an anti-inflammatory carboxylic pharmaceutical agent selected from the group consisting of (1) 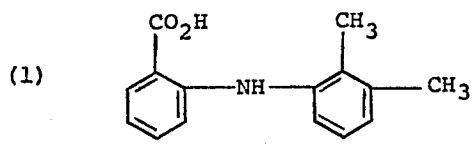

(2) 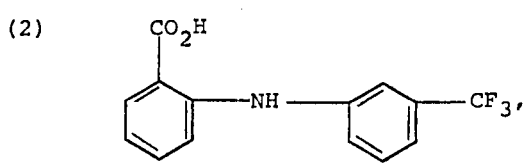

(3) 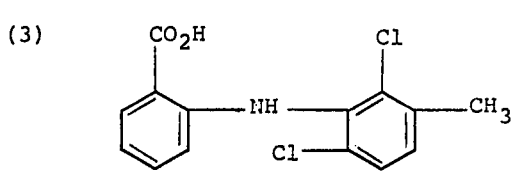

(4) 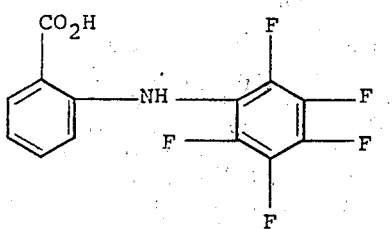

(5) 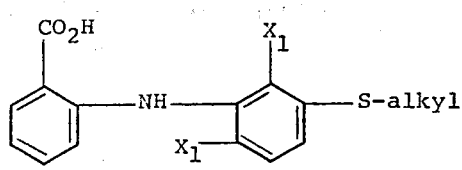

wherein $X_1$ represents Cl, Br, F or I and said alkyl has 1–3 carbon atoms, (6) 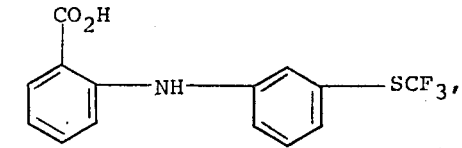

(7)

(8) 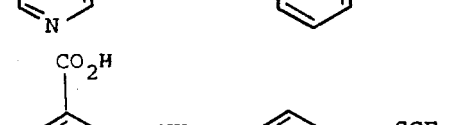

(9) 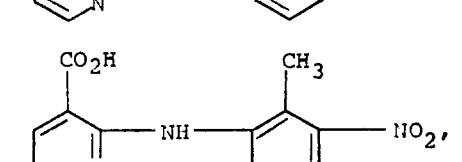

(10) 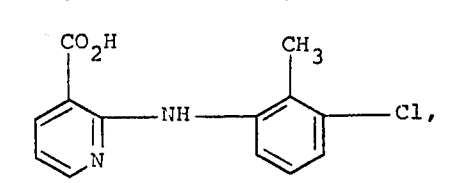

(11) 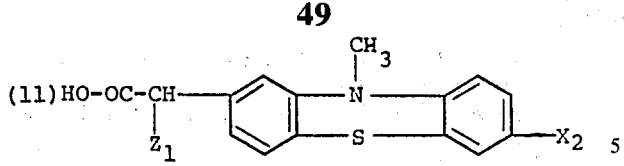

wherein $Z_1$ is selected from the group consisting of hydrogen and methyl, and $X_2$ is selected from the group consisting of hydrogen and methoxy,

(12) 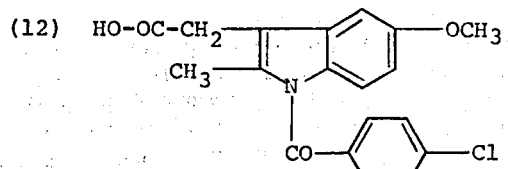

and

(13) 

2. The polymer of claim 1 having an average molecular weight between about 2,000 and 1,000,000.

3. The polymeric compound of claim 1 which is a copolymer further containing repeating units of the formula $$\left[ -CH_2-\underset{\underset{R_1}{|}}{\overset{\overset{R_7'}{|}}{C}}- \right]$$

wherein
$R_7'$ represents hydrogen and methyl and
$R_1$ represents a member selected from the group consisting of
a. —O—CO—$R_3$ wherein $R_3$ represents a saturated hydrocarbon chain having 8–18 carbon atoms,
b. —CO—O—$R_4$ wherein $R_4$ represents a saturated hydrocarbon chain having 8–18 carbon atoms or N,N'-dialkylamino-ethyl wherein said alkyl moieties have 1–3 carbon atoms,
c. —CH$_2$—O—CO—$R_5$ wherein $R_5$ is a saturated hydrocarbon having 2-18 carbon atoms and (d) 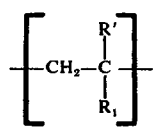

4. The polymeric compound of claim 3 having between 10 and 100% by weight, relative to the total weight of the polymer, of units substituted by the acyl residue of the anti-inflammatory pharmaceutical agent.

5. The polymeric compound of claim 3 wherein $R_1$ is selected from the group consisting of

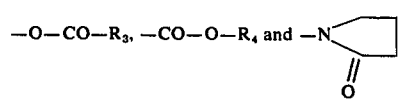

6. The polymeric compound of claim 1, wherein Z is the acyl residue of an acid of the formula

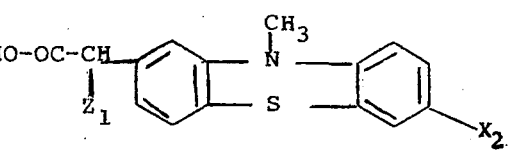

7. The polymeric compound of claim 1 wherein Z is the acid residue of an acid of the formula

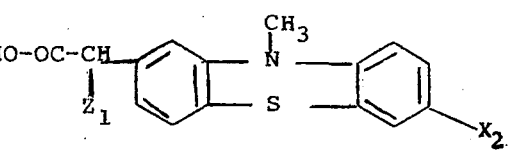

8. The polymeric compound of claim 1, wherein Z is the acid residue of an acid of the formula

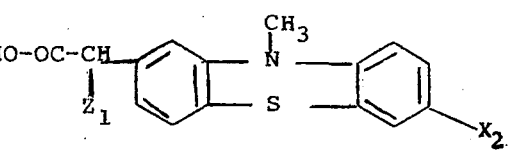

9. The polymeric compound of claim 1, wherein Z is the acid residue of an acid of the formula

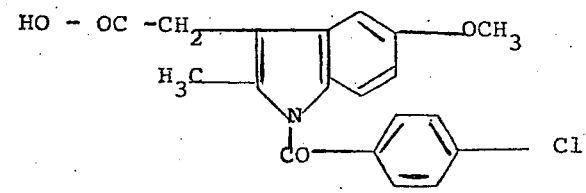

wherein $Z_1$ is hydrogen or methyl and $X_2$ is hydrogen or methoxy.

10. The polymeric compound of claim 1, wherein Z is the acyl residue of an acid of the formula

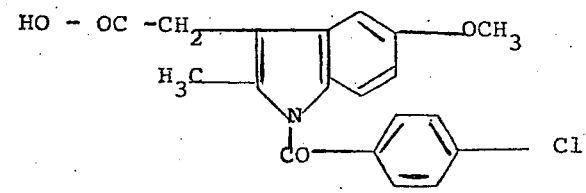

11. The polymeric compound of claim 1, wherein Z is the acyl residue of an acid of the formula

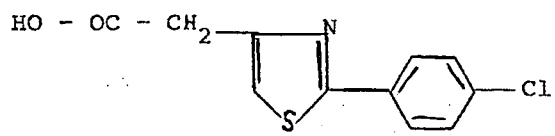

12. The polymeric compound of claim 1 wherein Z is the acyl residue of an acid of the formula

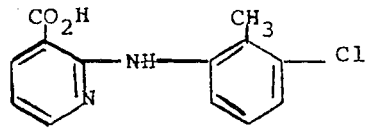

13. A polymeric compound containing repeating units of the formula

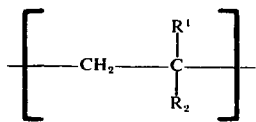

wherein $R^1$ and $R_2$ are selected from the group of values consisting of:
a. $R_2$ is $-[O-CO-CH_2]_n-O-Z$, $R^1$ is hydrogen and $n$ is 1-10,
b. $R_2$ is $-CH_2-O-CO-CH_2-O-Z$ and $R_1$ is hydrogen or methyl,
c. $R_2$ is $-CH_2-NH-CO-CH_2-O-Z$ and $R^1$ is hydrogen,
d. $R_2$ is $-CO-NH-CH_2-NH-CO-CH_2-O-Z$ and $R^1$ is hydrogen, and
e. $R_2$ is $-O-CO-CH_2-\overset{+}{\underset{r\ \ \ r'}{N}}(CH_2)_2-O-Z$, $Y^\ominus$ wherein $r$ and $r'$ represent alkyl having 1-3 carbon atoms, Y represents chlorine or bromine, and $R^1$ is hydrogen or methyl, and wherein Z is the acyl residue of an anti-inflammatory pharmaceutical agent whose molecule comprises a carboxylic acid function.

* * * * *

UNITED STATES PATENT OFFICE
CERTIFICATE OF CORRECTION

Patent No. 3,946,035        Dated   March 23, 1976

Inventor(s) Bernard Jacquet, et al

It is certified that error appears in the above-identified patent and that said Letters Patent are hereby corrected as shown below:

Claim 3, the first structural formula should read --

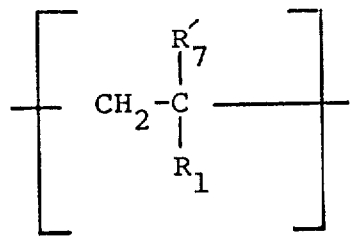

Signed and Sealed this

Fourteenth Day of September 1976

[SEAL]

Attest:

RUTH C. MASON
*Attesting Officer*

C. MARSHALL DANN
*Commissioner of Patents and Trademarks*